US011052136B2

(12) United States Patent
Badimon Maestro et al.

(10) Patent No.: US 11,052,136 B2
(45) Date of Patent: Jul. 6, 2021

(54) PREVENTION AND/OR TREATMENT OF ISCHEMIA OR ISCHEMIA/REPERFUSION INJURY

(71) Applicant: FUNDACIÓ INSTITUT DE RECERCA DE L'HOSPITAL DE LA SANTA CREU I SANT PAU, Barcelona (ES)

(72) Inventors: Lina Badimon Maestro, Barcelona (ES); Judit Cubedo Ràfols, Barcelona (ES); Gemma Vilahur Garcia, Barcelona (ES); Teresa Padró Capmany, Barcelona (ES)

(73) Assignee: FUNDACIÓ INSTITUT DE RECERCA DE L'HOSPITAL DE LA SANTA CREU I SANT PAU, Barcelona (ES)

( * ) Notice: Subject to any disclaimer, the term of this patent is extended or adjusted under 35 U.S.C. 154(b) by 71 days.

(21) Appl. No.: 16/084,521

(22) PCT Filed: Mar. 14, 2017

(86) PCT No.: PCT/EP2017/056027
§ 371 (c)(1),
(2) Date: Sep. 12, 2018

(87) PCT Pub. No.: WO2017/157958
PCT Pub. Date: Sep. 21, 2017

(65) Prior Publication Data
US 2019/0076509 A1    Mar. 14, 2019

(30) Foreign Application Priority Data

Mar. 14, 2016 (EP) ..................................... 16382111

(51) Int. Cl.
*A61K 38/46* (2006.01)
(52) U.S. Cl.
CPC .... *A61K 38/465* (2013.01); *C12Y 301/01002* (2013.01)
(58) Field of Classification Search
None
See application file for complete search history.

(56) References Cited

U.S. PATENT DOCUMENTS

| 5,262,165 A | 11/1993 | Govil et al. |
| 5,948,433 A | 9/1999 | Burton et al. |
| 6,010,715 A | 1/2000 | Wick et al. |
| 6,071,531 A | 6/2000 | Jona et al. |

FOREIGN PATENT DOCUMENTS

| EP | 2716300 A1 | 4/2014 |
| WO | 2011033511 A1 | 3/2011 |
| WO | 2013003593 A1 | 1/2013 |
| WO | 2015140348 A2 | 9/2015 |

OTHER PUBLICATIONS

Jeong et al. 2012; Protective effects of transduced Tat-DJ-1 protein against oxidative stress and ischemic brain injury. Experimental and Molecular Medicine. 44(10); 586-593.*
Yanagisawa et al. 2008; DJ-1 protects against neurodegeneration caused by focal cerebral ischemia and reperfusion in rats. Journal of Cerebral Blood Flow & Metabolism. 28: 563-578.*
Dongworth et al. 2014; DJ-1 protects against cell death following acute cardiac ischemia-reperfusion injury. Cell Death and Disease. 5:e1082, pp. 1-7.*
Altschul et al., "Gapped BLAST and PSI-BLAST: a New Generation of Protein Database Search Programs", Nucleic Acid Research, 1997, pp. 3389-3402, vol. 25, No. 17.
Altschul et al., "Local Alignment Statistics", Methods in Enzymology, 1996, pp. 460-480, vol. 266.
Altschul, "Amino Acid Substitution Matrices from an Information Theroretic Perspective", Journal of Molecular Biology, 1991, pp. 555-565, vol. 219.
Bayes-Genis et al., "Human Progenitor Cells Derived from Cardiac Adipose Tissue Ameliorate Myocardial Infarction in Rodents", Journal of Molecular and Cellular Cardiology, 2010, pp. 771-780, vol. 49.
Cung et al., "Cyclosporine before PCI in Patients with Acute Myocardial Infarction", New England Journal of Medicine, 2015, pp. 1021-1031, vol. 373.
Database WPI Week 201351 Thomson Scientific, London, GB; AN 20 13-G22445 & KR 2013 0037271 A.
Database WPI Week 201424 Thomson Scientific, London, GB; AN 2013-W03782 & KR 2013 0125630 A.
Edgar et al., "Gene Expression Omnibus: NCBI Gene Expression and Hybridization Array Data Repository", Nucleic Acids Research, 2002, pp. 207-210, vol. 30, No. 1.
Fishbein et al., "Early Phase Acute Myocardial Infarct Size Quantification: Validation of the Triphenyl Tetrazolium Chloride Tissue Enzyme Staining Technique", American Heart Journal, 1981, pp. 593-600, vol. 101, No. 5.
Grande et al., "Estimation of Acute Myocardial Infarct Size in Man by Serum CK-MB Measurements", Circulation, 1982, pp. 756-764, vol. 65, No. 4.

(Continued)

*Primary Examiner* — Karen Cochrane Carlson
(74) *Attorney, Agent, or Firm* — Thompson Coburn LLP; William A. Holtz

(57) ABSTRACT

The present invention relates to pharmaceutical compositions comprising a compound selected from the group consisting of: a) a polypeptide of SEQ ID NO:1, b) a functionally equivalent variant of the polypeptide according to a), c) a polynucleotide encoding a) or b), d) a vector comprising a polynucleotide according to c), e) a cell capable of secreting into the medium a polypeptide according to a) or b), and f) a nanoparticle comprising the polypeptide according to a) or b) and a pharmaceutically acceptable excipient. The invention also relates to the use of said compounds or pharmaceutical compositions for treatment and/or prevention of ischemia injury or ischemia/reperfusion injury in a subject.

22 Claims, 19 Drawing Sheets

Specification includes a Sequence Listing.

(56) References Cited

OTHER PUBLICATIONS

Hausenloy et al., "Ischemic Preconditioning Protects by Activating Prosurvival Kinases at Reperfusion", American Journal of Physiology Heart and Circulation Physiology, 2005, vol. 288, No. 2.

Karlin et al., "Applications and Statistics for Multiple High-Scoring Segments in Molecular Sequences", Proceedings of the National Academy of Science of the United States of America, 1993, pp. 5873-5877, vol. 90.

Karlin et al., "Methods for Assessing the Statistical Significance of Molecular Sequence Features by Using General Scoring Schemes", Proceedings of the National Academy of Sciences of the United States of America, 1990, pp. 2264-2268, vol. 87.

Kilkenny et al., "Improving Bioscience Research Reporting: The ARRIVE Guidelines for Reporting Animal Research", PLoS Biology, 2010, vol. 8, No. 6.

Kwon et al., "Novel Glyoxalases from *Arabidopsis thaliana*", FEBS Journal, 2013, pp. 3328-3339, vol. 280.

Lacerda et al., "Ischaemic Postconditioning Protects Against Reperfusion Injury via the SAFE Pathway", Cardiovascular Research, 2009, pp. 201-208, vol. 84.

Myers et al., "Optimal Alignments in Linear Space", Computer Applications in the Biosciences, 1988, pp. 11-17, vol. 4, No. 1.

Needleman et al., "A General Method Applicable to the Search for Similarities in the Amino Acid Sequence of Two Proteins", Journal of Molecular Biology, 1970, pp. 443-453, vol. 48.

Smith et al., "Comparison of Biosequences", Advances in Applied Mathematics 2, 1981, pp. 484-489.

Takagawa et al., "Myocardial Infarct Size Measurement in the Mouse Chronic Infarction Model: Comparison of Area- and Length-Based Approaches", Journal of Applied Physiology, 2007, pp. 2104-2111, vol. 102.

Tsang et al., "Postconditioning: A Form of "Modified Reperfusion" Protects the Myocardium by Activating the Phosphatidylinositol 3-Kinase-Akt Pathway", Circulation Research Journal of the American Heart Association, 2004, pp. 230-232, vol. 95.

Vilahur et al., "Reperfusion-Triggered Stress Protein Response in the Myocardium is Blocked by Post-Conditioning. Systems Biology Pathway Analysis Highlights the Key Role of the Canonical Aryl-Hydrocarbon Receptor Pathway", European Heart Journal, 2012, pp. 2082-2093, vol. 34, No. 27.

\* cited by examiner

PREVENTION AND/OR TREATMENT OF ISCHEMIA OR ISCHEMIA/REPERFUSION INJURY

CROSS-REFERENCE TO RELATED APPLICATIONS

This application is a U.S. National Phase Application under 35 U.S.C. § 371 of International Patent Application No. PCT/EP2017/056027, filed Mar. 14, 2017, which claims priority to European Patent Application No. 16382111.9, filed Mar. 14, 2016, all of which are incorporated herein by reference in their entireties.

FIELD OF THE INVENTION

The present invention relates, in general, to the prevention and/or treatment of ischemia injury or ischemia/reperfusion injury.

BACKGROUND OF THE INVENTION

During ischemia important changes occur in cardiac energy metabolism due to the reduced oxygen availability. Ischemia triggers mitochondrial injury, increases reactive oxidative species (ROS) generation, and oxidative DNA damage. Fast reperfusion is the optimal way to rescue the ischemic heart, however, the process is associated with cellular damage by activation of deleterious signaling cascades which may cause cardiomyocyte damage eventually increasing infarct size. The imbalance between oxygen supply and consumption during ischemia and reperfusion induces modifications in cardiomyocyte structure and function through coordinated changes in gene and protein expression, and in the activity of a variety of proteins.

Mitochondria (mit) are the main source of ATP through oxidative phosphorylation via the electron transport chain. Because of the energy requirements of the heart the role of mit is crucial, in fact they represent nearly one-third of its total mass. The correct maintenance of mit-homeostasis is essential for cell survival because mits are potent sources of free radicals and proapoptotic factors, but they can also reduce the detrimental effects of an excessive oxidative stress. Myocardial ischemia affects the electron transport chain leading to an increase in cardiomyocyte death during reperfusion. Experimental approaches have demonstrated that chemical blockade of electron transport during ischemia inhibits the opening of the mitochondrial permeability transition pore (MPTP) decreasing cardiomyocyte injury during reperfusion. Ischemic post-conditioning (IPost-Co), brief episodes of myocardial ischemia/reperfusion applied at the time of reperfusion after a prolonged ischemic insult, has revealed to activate intrinsic pro-survival signaling cascades limiting reperfusion injury and reducing infarct size. There are several studies supporting changes in specific protective pathways during IPost-Co such as the activation of Reperfusion Injury Salvage Kinases (RISK) (Tsang A Circ Res 2004; 95:230-2; Hausenloy D J, Am J Physiol Heart Circ Physiol 2005; 288:H971-6) or the prosurvival Survivor Activating Factor Enhancement (SAFE) (Lacerda L, Cardiovasc Res 2009; 84:201-8). In addition, it has been recently reported that the down-regulation of the aryl-hydrocarbon receptor (AhR) signaling pathway seems to contribute to the cardioprotective effects afforded by IPost-Co (Vilahur G, Eur Heart J 2012; 34:2082-2093). The controversial results obtained in clinical trials testing cardioprotection against ischemia and direct reperfusion injury (IdR) (Cung T T, N Engl J Med 2015; 373(11):1021-31), have highlighted the need of further research to uncover mechanisms yet unknown.

Effective therapies to reduce or prevent ischemia/reperfusion injury have proven elusive. Despite an improved understanding of the pathophysiology of this process and encouraging preclinical trials of multiple agents, most of the clinical trials to prevent reperfusion injury have been disappointing. Therefore, in view of the state of the art, there is still a need to develop strategies to prevent damages caused by ischemia/reperfusion.

SUMMARY OF THE INVENTION

In a first aspect, the invention relates to a pharmaceutical composition comprising a compound selected from the group consisting of:
  a) a polypeptide of SEQ ID NO:1,
  b) a functionally equivalent variant of the polypeptide according to a),
  c) a polynucleotide encoding a) or b),
  d) a vector comprising a polynucleotide according to c),
  e) a cell capable of secreting into the medium a polypeptide according to a) or b), and
  f) a nanoparticle comprising the polypeptide according to a) or b)
and a pharmaceutically acceptable excipient.

In a second aspect, the invention relates to a compound selected from the group consisting of:
  a) a polypeptide of SEQ ID NO:1,
  b) a functionally equivalent variant of the polypeptide according to a),
  c) a polynucleotide encoding a) or b),
  d) a vector comprising a polynucleotide according to c),
  e) a cell capable of secreting into the medium a polypeptide according to a) or b), and
  f) a nanoparticle comprising the polypeptide according to a) or b) or a pharmaceutical composition according to the invention for use in medicine.

In a third aspect, the invention relates to a compound selected from the group consisting of:
  a) a polypeptide of SEQ ID NO:1,
  b) a functionally equivalent variant of the polypeptide according to a),
  c) a polynucleotide encoding a) or b),
  d) a vector comprising a polynucleotide according to c),
  e) a cell capable of secreting into the medium a polypeptide according to a) or b), and
  f) a nanoparticle comprising the polypeptide according to a) or b)
or a pharmaceutical composition according to the invention for use in the treatment and/or prevention of ischemia injury or ischemia/reperfusion injury in a subject.

Kruskal-Wallis; § P<0.05 vs. sham-operated animals; †P<0.05 vs. ischemia; and ‡P<0.05 vs. IdR; Mann-Whitney; n≥5/group). Box plot showing changes between groups in peroxiredoxin-6 (PRDX6) (C) spot intensity (†P<0.05 IPost-Co vs. ischemia; Mann-Whitney; n≥3/group); and (D) gene expression levels (*P<0.001 Kruskal-Wallis; § P<0.05 vs. sham-operated animals; †P<0.05 vs. ischemia; and ‡P<0.05 vs. IdR; Mann-Whitney; n≥5/group).

Figure 3:
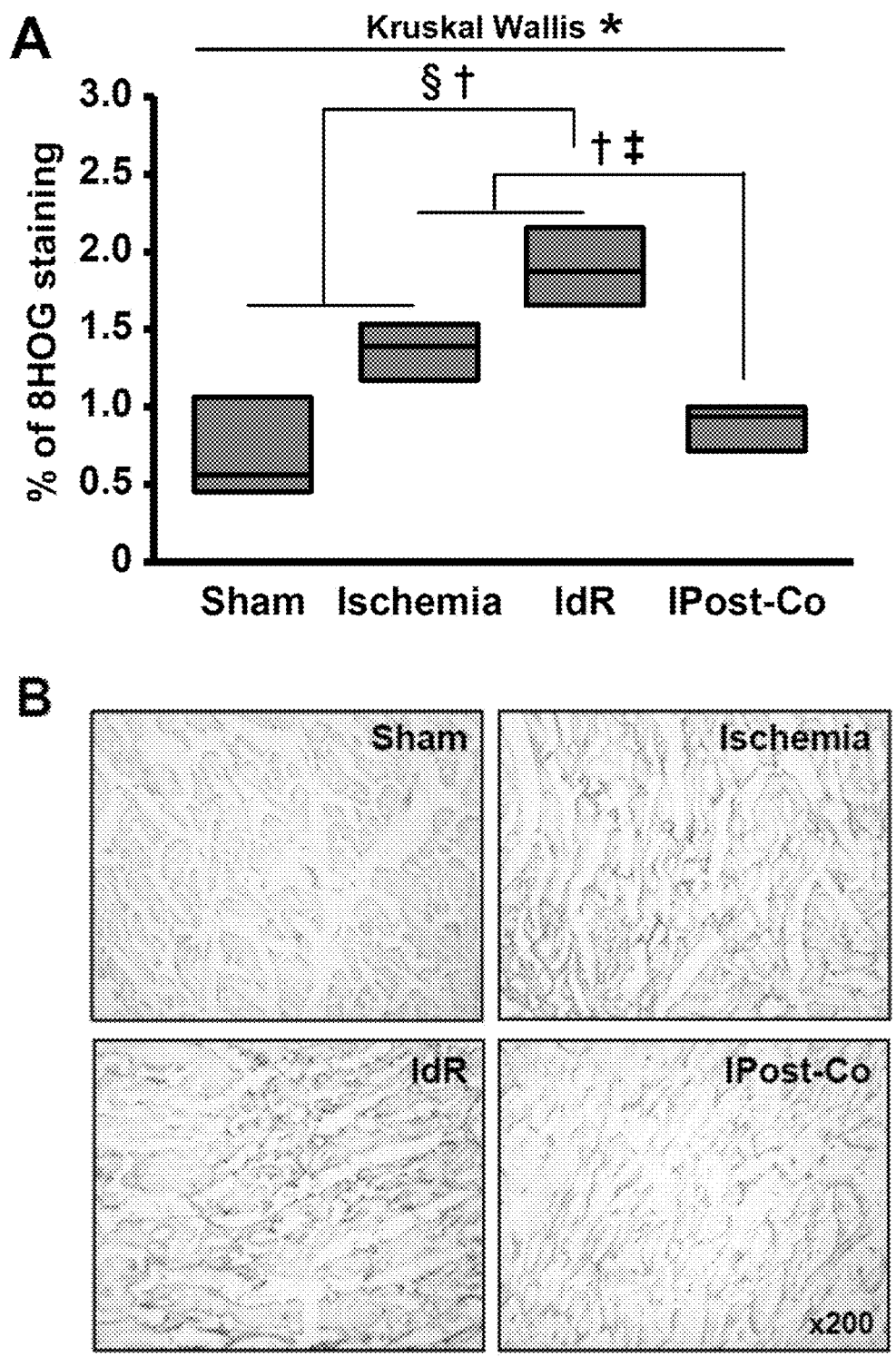
Figure 3:
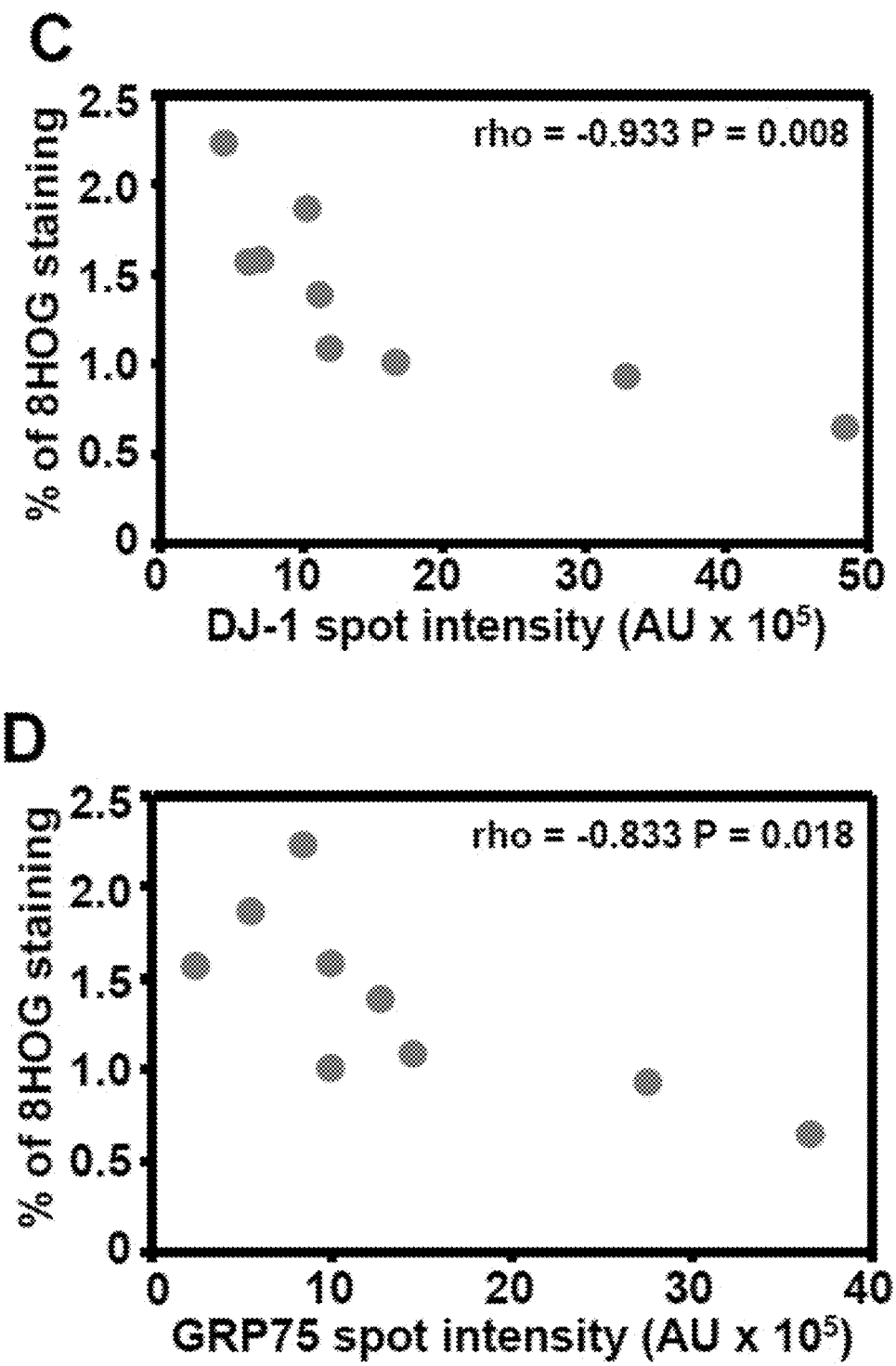
Figure 3:
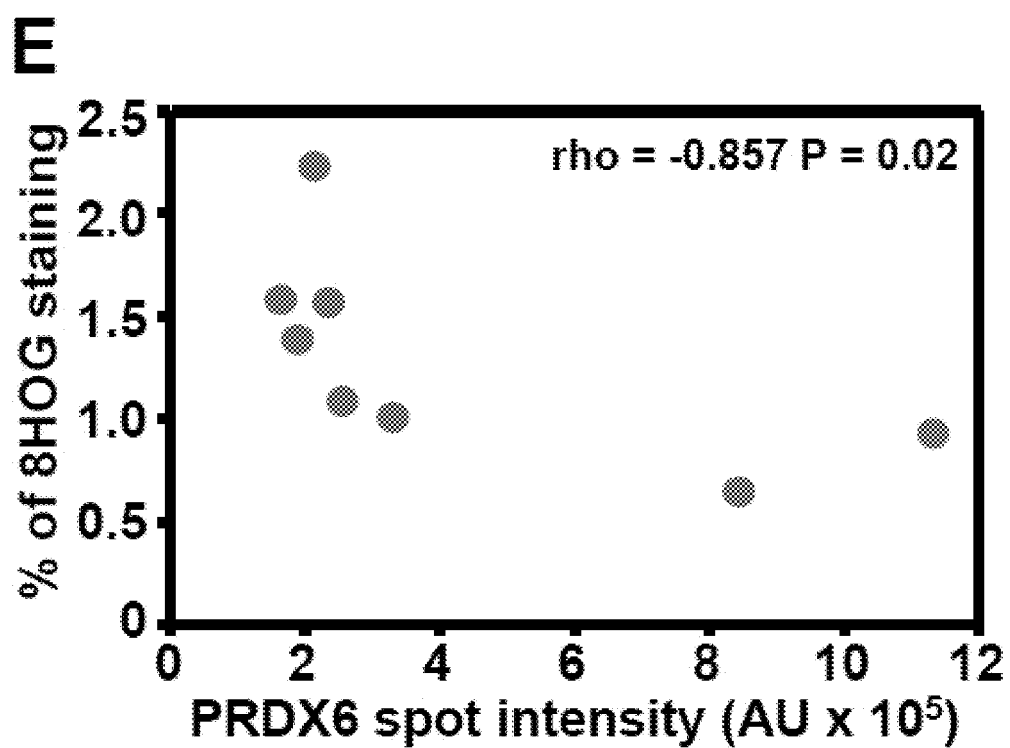

FIG. 3. Oxidative stress levels in the porcine model of MI. (A) Box-plot sowing the levels of 8-hydroxyguanosine (8HOG) as a marker of oxidative stress (*P<0.001 Kruskal-Wallis; § P<0.05 vs. sham-operated animals; †P<0.05 vs. ischemia; and ‡P<0.05 vs. IdR; Mann-Whitney; n≥3/group). (B) Representative immunohistochemistry images showing 8HOG content in porcine myocardial samples of the different groups. Scatter plots showing the inverse correlation of DJ-1 (C), GRP75 (D) and PRDX6 (E) spot intensity in the 2-DE analysis with 8HOG myocardial content (Spearman correlation).

Figure 4:
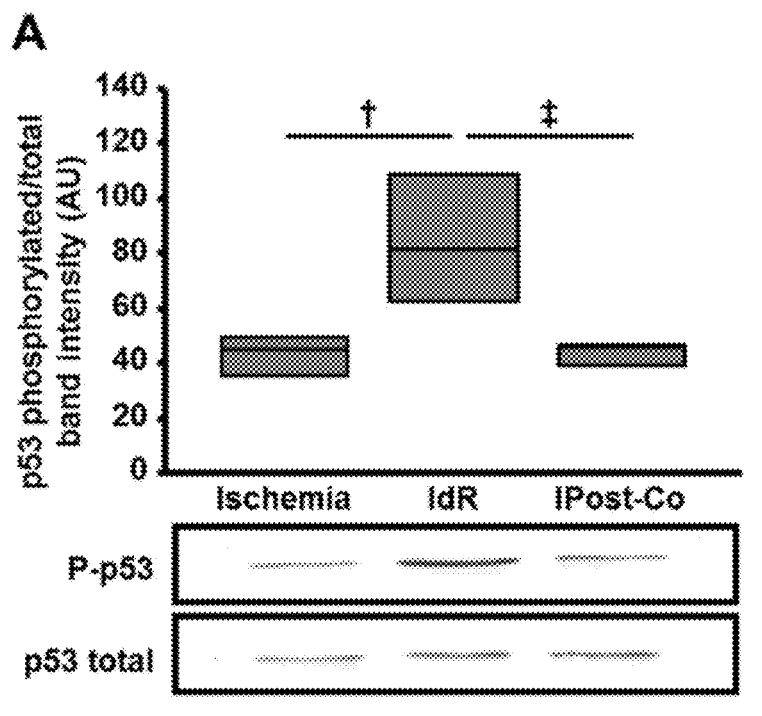
Figure 4:
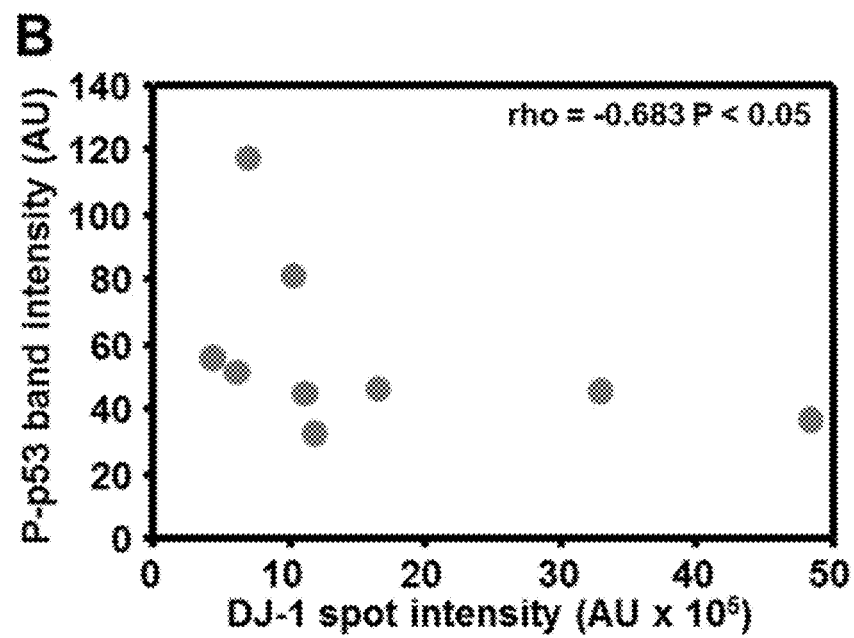
Figure 4:
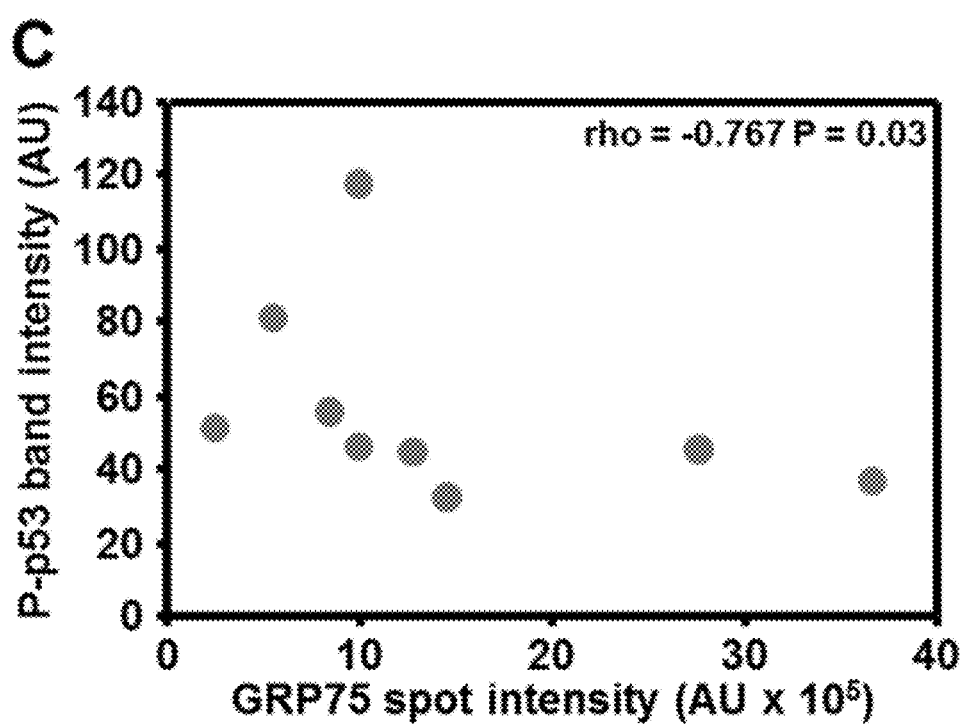

FIG. 4. Correlation of DJ-1 and GRP75 with the apoptosis marker p53. (A) Box-plot and WB representative image showing the significant increase in the levels of phosphorylated p53 in the myocardium of animals subjected to IdR (†P<0.05 vs. ischemia; ‡P<0.05 vs. IdR). Scatter plots showing the inverse correlation of DJ-1 (B) and GRP75 (C) spot intensity in the 2-DE analysis with phosphorylated p53 analyzed by WB analysis (Spearman correlation).

Figure 5:
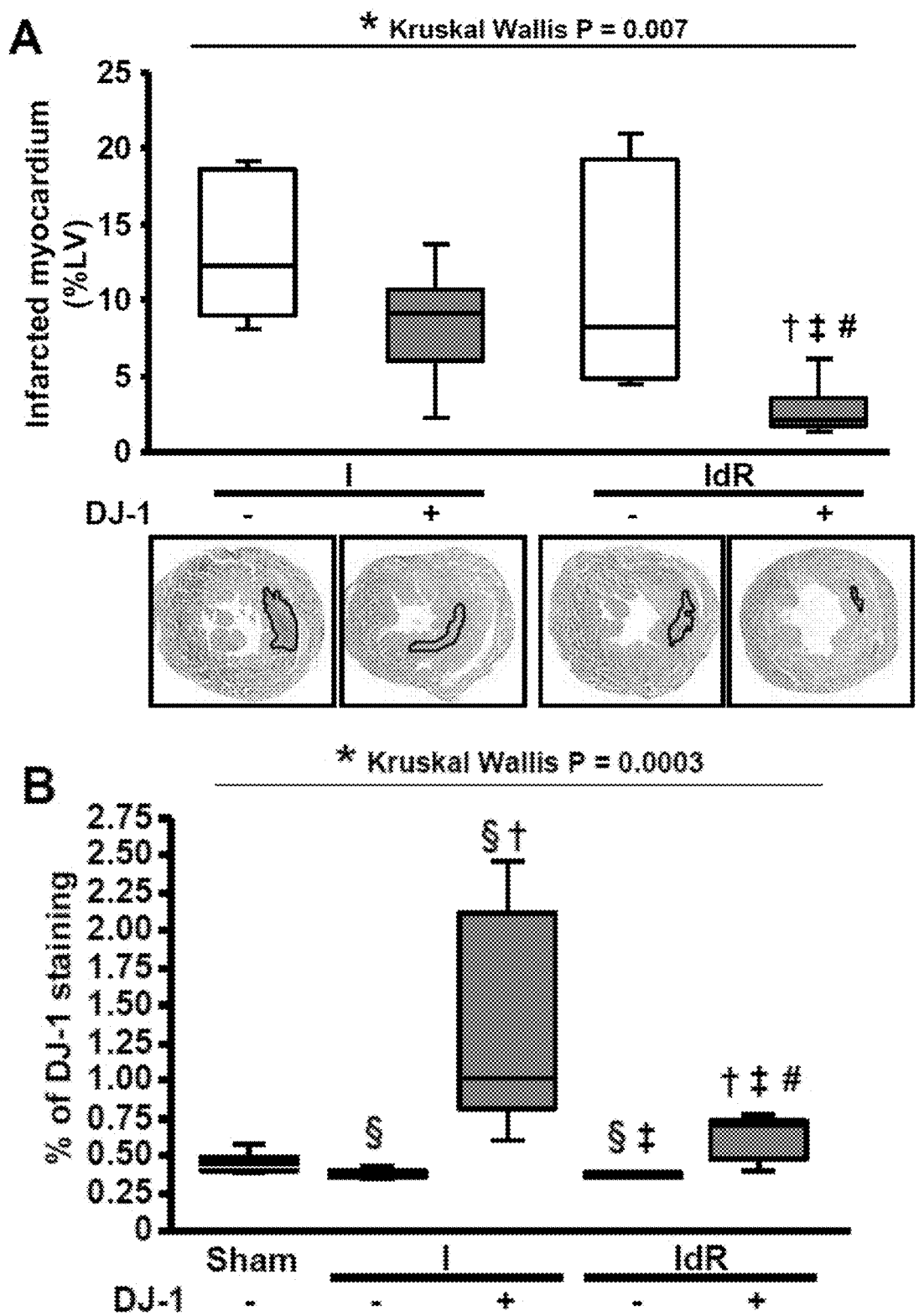

FIG. 5. Effects of systemic administration of DJ-1 on infarct size in the MI mouse model. (A) Box-plot diagram and representative immunohistochemistry images showing changes in the percentage of left ventricular infarcted myocardium, and (B) box-plot diagram showing changes in DJ-1 detection in the myocardium after DJ-1 administration in the mouse model of MI (*P<0.05 Kruskal-Wallis; § P<0.05 vs. sham; †P<0.05 vs. ischemia; ‡P<0.05 vs. ischemia+DJ-1; #P<0.05 vs. IdR; Mann-Whitney; n≥5/group).

Figure 6:
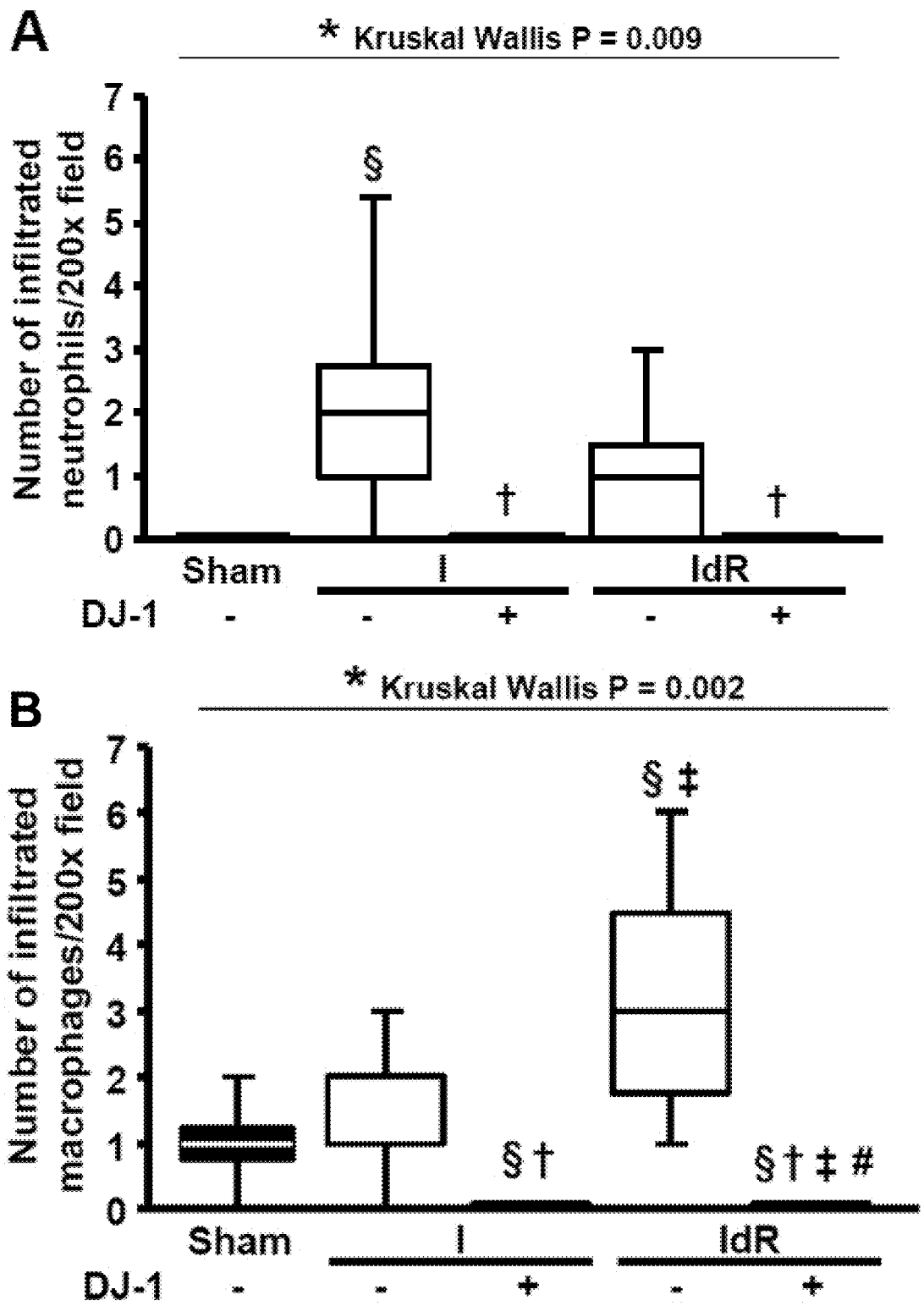

FIG. 6. Effects of systemic administration of DJ-1 on the infiltration of leukocytes in the MI mouse model. Box-plot diagrams showing changes in neutrophils (A) and macrophages (B) infiltration in the myocardium after DJ-1 administration in the mouse model of MI (*P<0.05 Kruskal-Wallis; § P<0.05 vs. sham; †P<0.05 vs. ischemia; ‡P<0.05 vs. ischemia+DJ-1; #P<0.05 vs. IdR; Mann-Whitney; n≥5/group).

Figure 7:
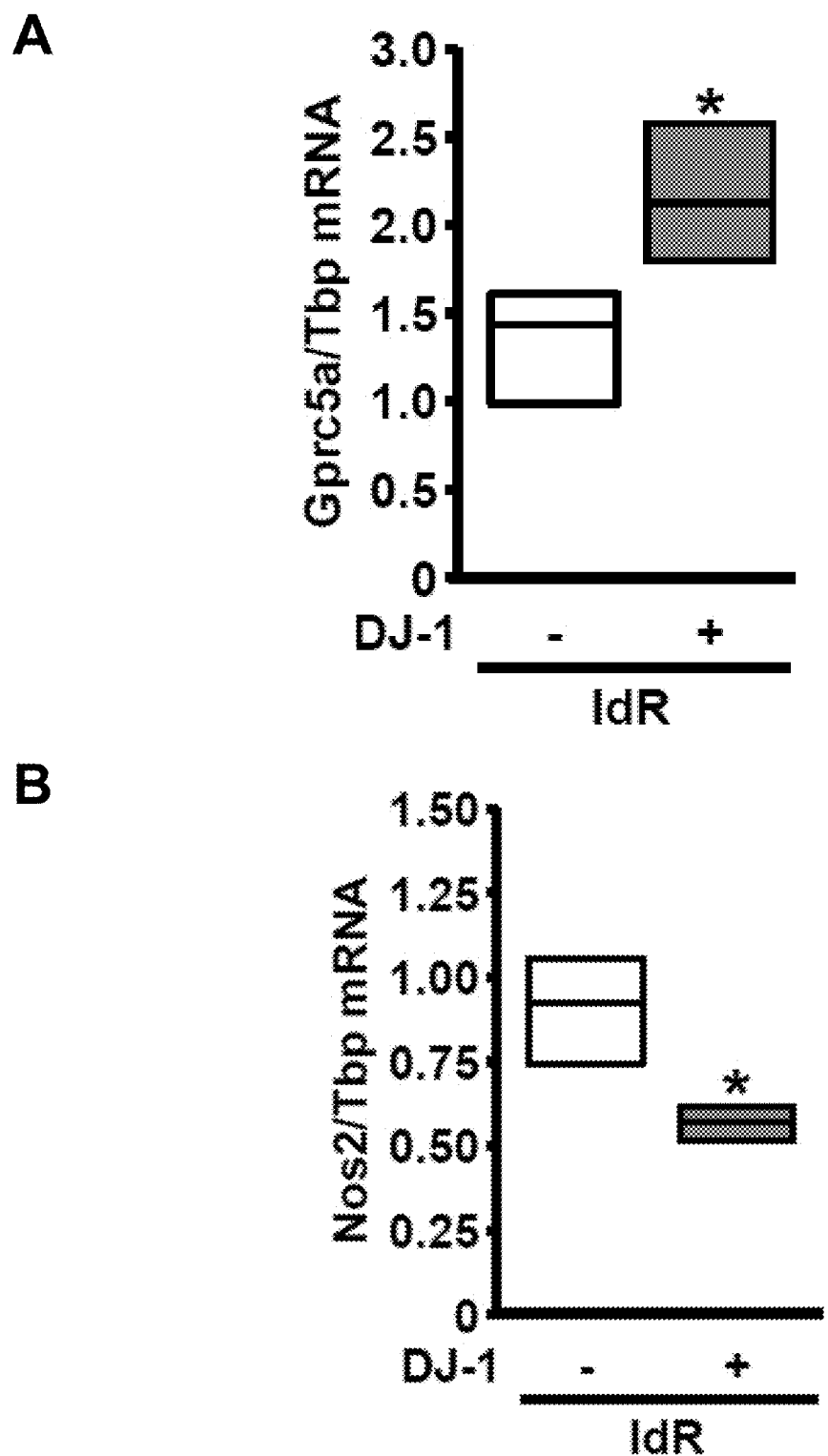
Figure 7:
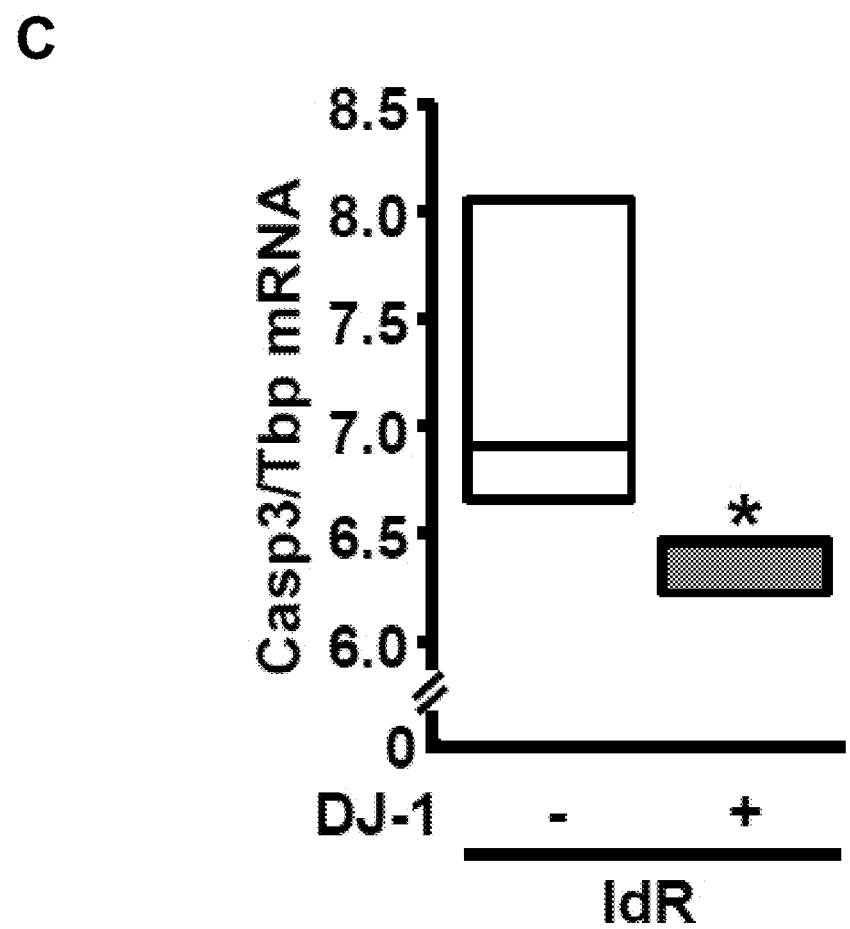

FIG. 7. Box-plot showing the significant changes in Gprc5a (A), Nos2 (B), and caspase-3 (C) gene expression after DJ-1 pre-treatment in the mouse model of IdR (*P<0.05; Mann-Whitney; n=4/group).

Figure 8:
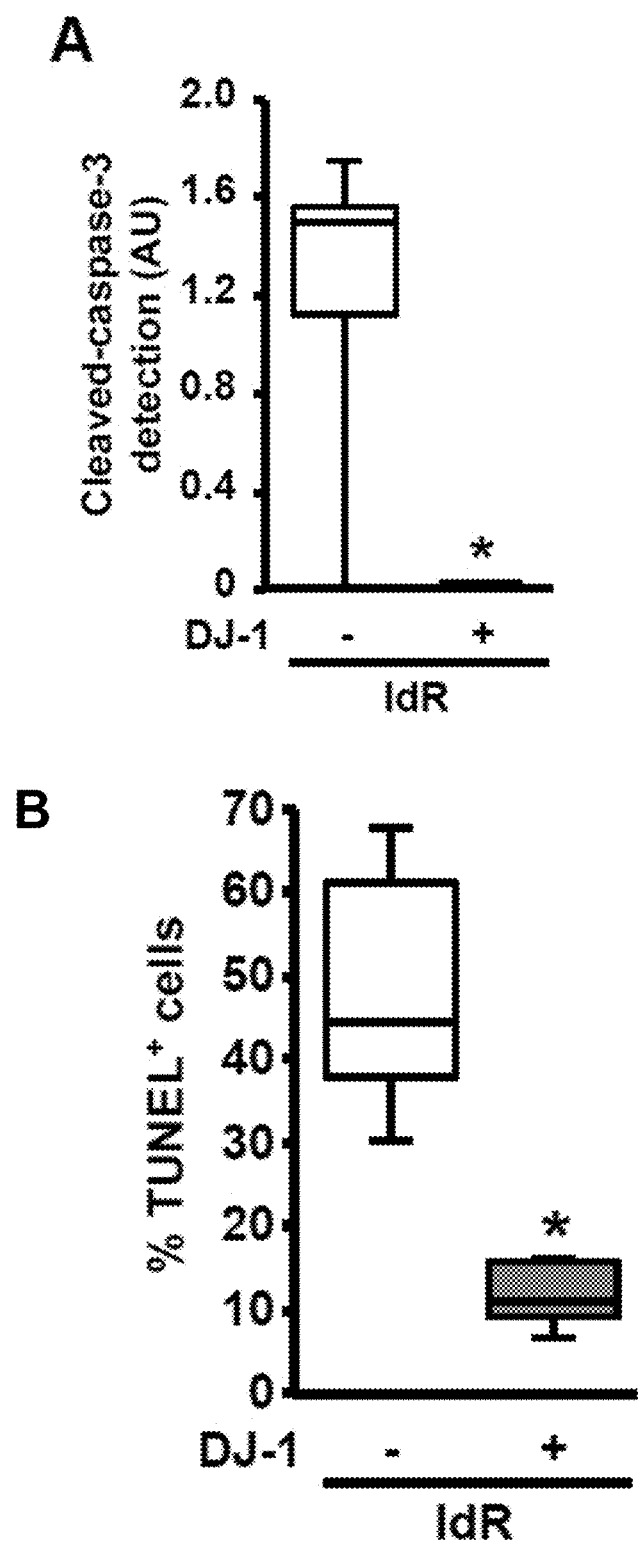

FIG. 8. Changes in apoptosis after systemic administration of DJ-1 in the MI mouse model. Box-plots showing (A) the significant decrease in cleaved caspase-3 detection in immunohistochemistry analysis after DJ-1 pre-treatment in mice subjected to IdR; and (B) the significant decrease in the detection of TUNEL positive cells in the myocardium of animals subjected to IdR after DJ-1 pre-treatment. *P<0.05; Mann-Whitney; n=4/group.

Figure 9:
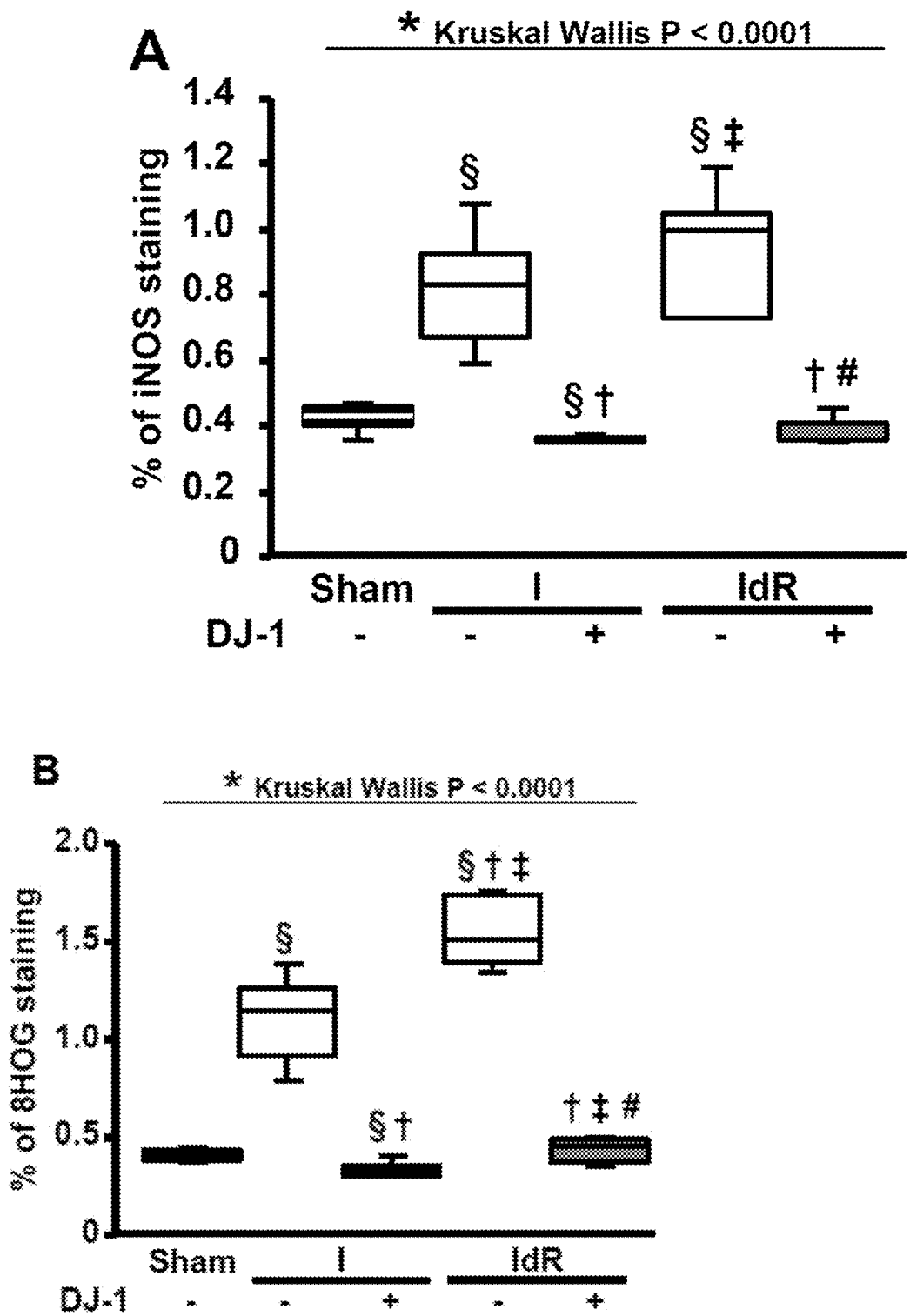
Figure 9:
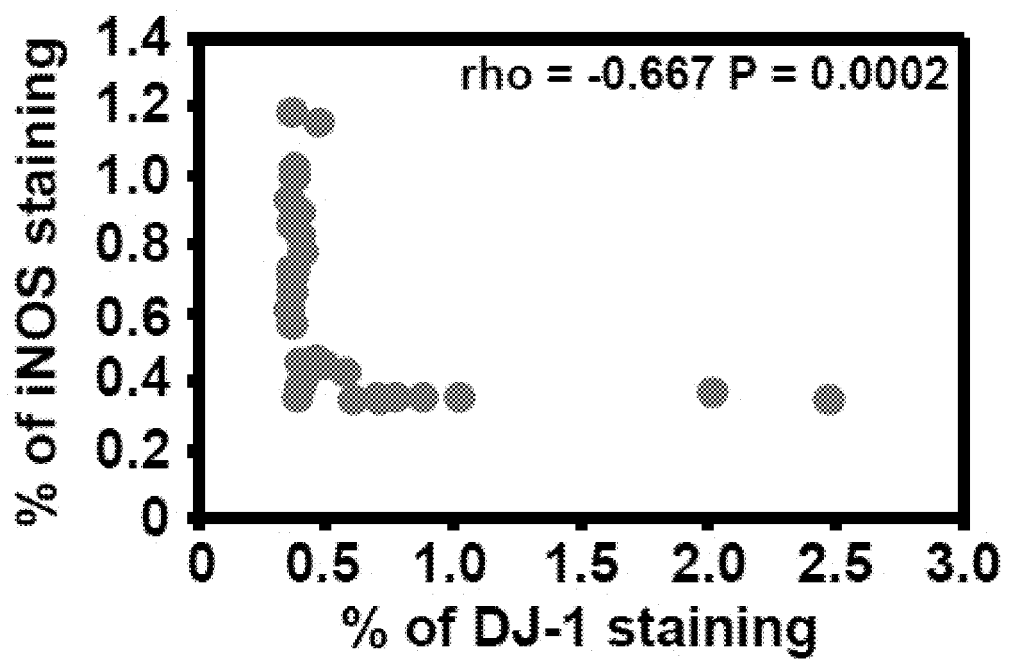
Figure 9:
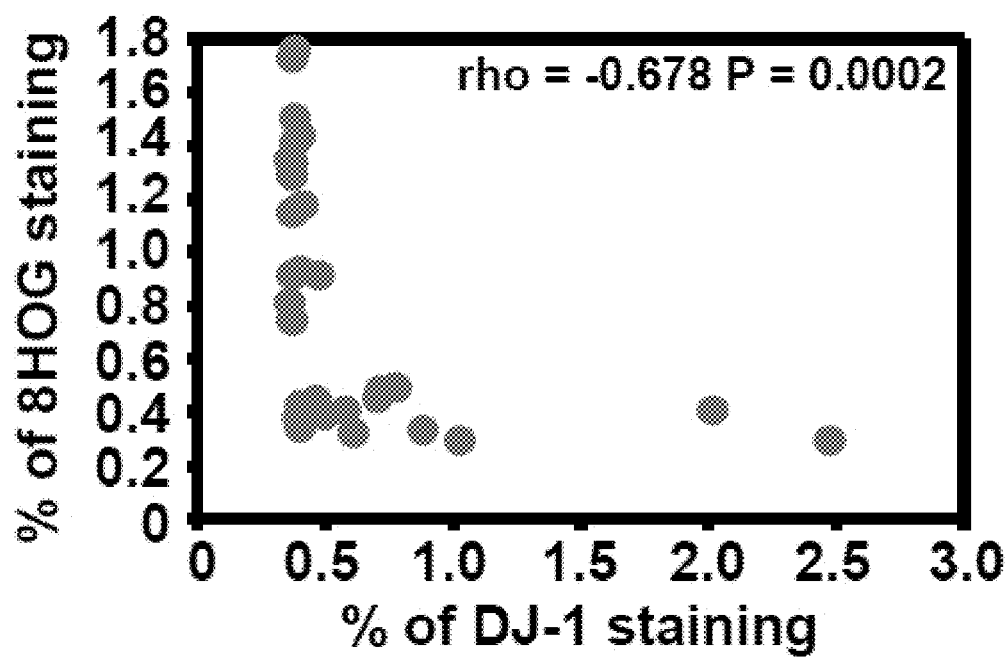
Figure 9:
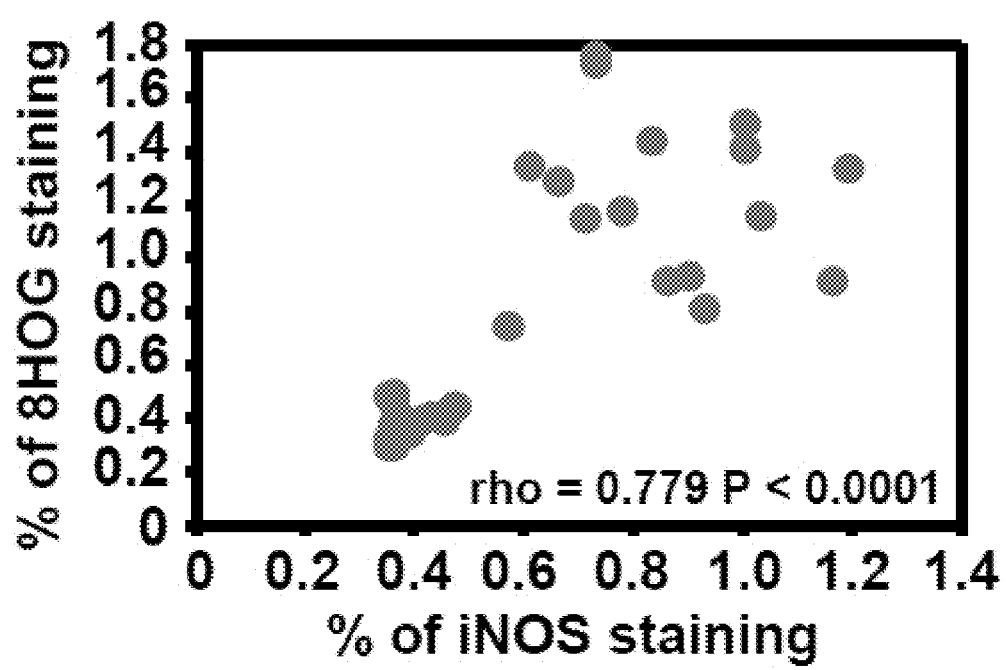

FIG. 9. Oxidative stress-related effects of systemic administration of DJ-1 in the MI mouse model. Box-plot diagrams showing changes in iNOS (A) and 8-hydroxyguanosine (8HOG; B) content in the myocardium after DJ-1 administration in the mouse model of MI (*P<0.05 Kruskal-Wallis; § P<0.05 vs. sham; †P<0.05 vs. ischemia; ‡P<0.05 vs. ischemia+DJ-1; #P<0.05 vs. IdR; Mann-Whitney; n≥5/group). Scatter plots showing the inverse correlation of DJ-1 with iNOS (C) and 8HOG (D), and the positive correlation between iNOS and 8HOG (E) in the myocardium of the mouse model of MI (Spearman correlation).

Figure 10:
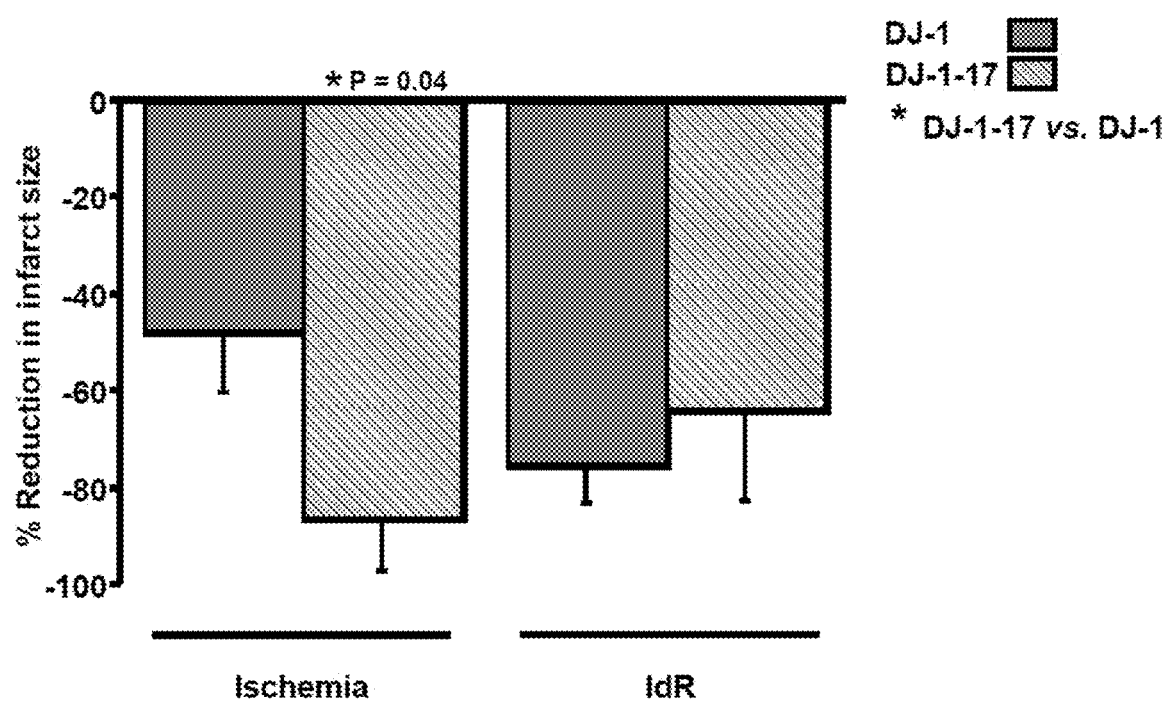

FIG. 10. Differential effects of systemic administration of full length DJ-1 and truncated DJ-1-17 on infarct size reduction in the MI mouse model. Bar diagram (mean±SEM) showing the percentage of reduction in infarct size after pre-treatment with full length DJ-1 and truncated DJ-1-17 recombinant peptides in animals subjected to ischemia and IdR. *P=0.04; Mann-Whitney truncated DJ-1-17 vs. full length DJ-1.

Figure 11:
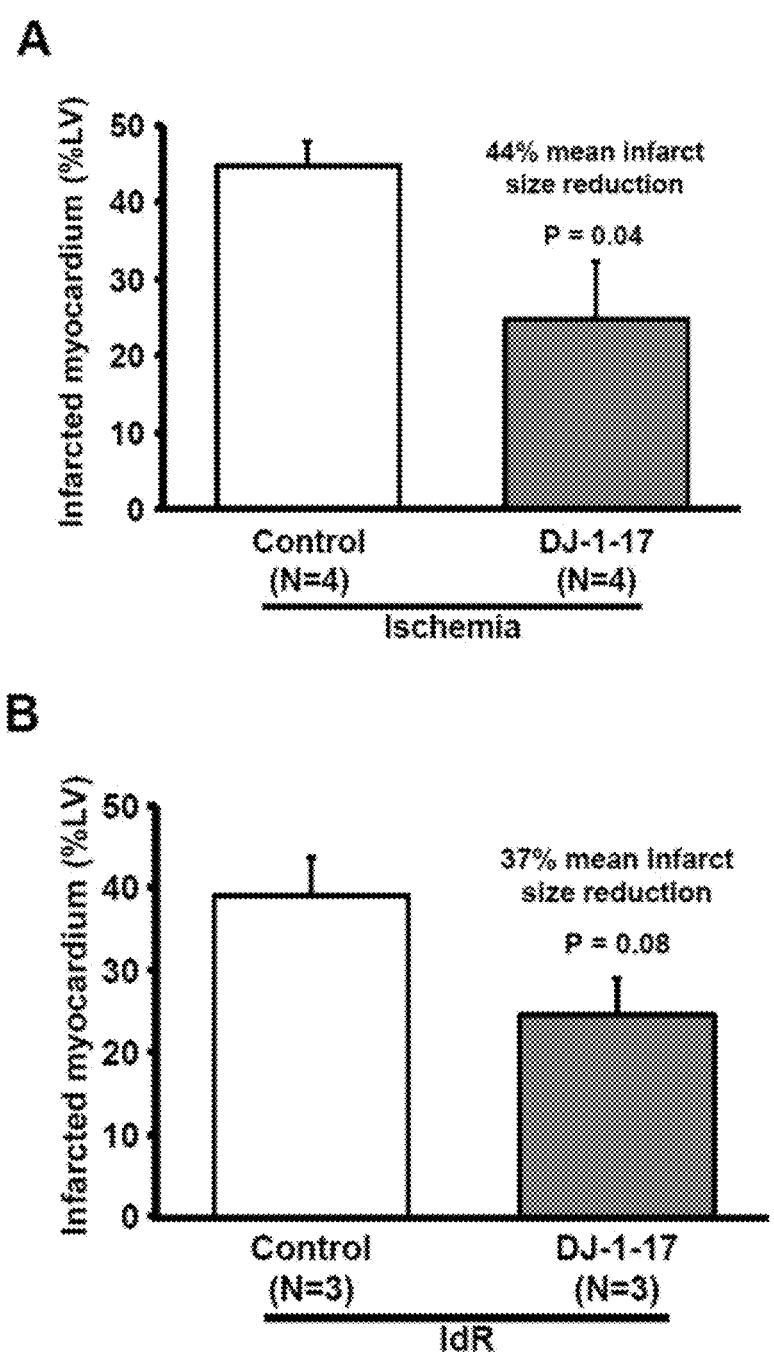

FIG. 11. Effects of systemic administration of DJ-1-17 on infarct size in the MI rat model. (A) Bar diagram showing the DJ-1-17-induced decrease in the percentage of left ventricular infarcted myocardium after 45 min of ischemia (P=0.04; T-test; n=4/group); and (B) bar diagram showing the DJ-1-17-induced decrease in the percentage of left ventricular infarcted myocardium after 45 min of ischemia and 7 days of reperfusion (P=0.08; T-test; n=3/group).

DETAILED DESCRIPTION OF THE INVENTION

The inventors have demonstrated the implication of DJ-1 in IPost-Co mediated cardioprotection (Examples 4 and 5). The administration of DJ-1 in a mouse model has revealed its clear cardioprotective effect against IdR injury through a multigenic response mainly mediated by G protein-coupled receptors, such as Gprc5a (Example 7). The inventors have also observed that the administration of a truncated DJ-1 form lacking the last 15 amino acids of the C-terminal domain of the protein sequence in a mouse model of myocardial infarction, induces a strongest protection against ischemia than the full length variant (Example 9).

Pharmaceutical Composition

In a first aspect, the invention relates to a pharmaceutical composition comprising a compound selected from the group consisting of:
a) a polypeptide of SEQ ID NO:1,
b) a functionally equivalent variant of the polypeptide according to a),
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

and a pharmaceutically acceptable excipient.

The term "pharmaceutical composition", as used herein, refers to a composition comprising a therapeutically effective amount of the agent according to the present invention and at least one pharmaceutically acceptable excipient. Pharmaceutical compositions according to the invention can be prepared, for instance, as injectables such as liquid solutions, suspensions, and emulsions.

"SEQ ID NO: 1" relates to the sequence of DJ-1 lacking its last 15 amino acids of the C-terminal domain. DJ1, as used herein, relates to a protein deglycase, a protein that repairs methylglyoxal- and glyoxal-glycated amino acids and proteins, and releases repaired proteins and lactate or glycolate, respectively. The sequence of DJ-1 in humans corresponds to the sequence in the UniProt database Q99497 9 Dec. 2015.

SEQ ID NO: 1
MASKRALVILAKGAEEMETVIPVDVMRRAGIKVTVAGLAGKDPVQCSRDV

VICPDASLEDAKKEGPYDVVVLPGGNLGAQNLSESAAVKEILKEQENRKG

```
LIAAICAGPTALLAHEIGFGSKVTTHPLAKDKMMNGGHYTYSENRVEKDG

LILTSRGPGTSFEFALAIVEALNG
```

"Functionally equivalent variant" is understood to mean all those proteins derived from the sequence SEQ ID NO: 1, by modification, substitution, insertion and/or deletion of one or more amino acids, whenever the function is substantially maintained. The functionally equivalent variant does not consist, consist essentially of or comprise the sequence shown in SEQ ID NO: 2.

```
                                              SEQ ID NO: 2
MASKRALVILAKGAEEMETVIPVDVMRRAGIKVTVAGLAGKDPVQCSRDV

VICPDASLEDAKKEGPYDVVVLPGGNLGAQNLSESAAVKEILKEQENRKG

LIAAICAGPTALLAHEIGFGSKVTTHPLAKDKMMNGGHYTYSENRVEKDG

LILTSRGPGTSFEFALAIVEALNGKEVAAQVKAPLVLKD
```

Preferably, variants of SEQ ID NO:1 are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from SEQ ID NO: 1 fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

The variants of SEQ ID NO: 1 may be both natural and artificial. The expression "natural variant" relates to all those variants of human SEQ ID NO: 1 which appear naturally in other species, i.e. the orthologues of SEQ ID NO: 1.

A functionally equivalent variant of SEQ ID NO: 1 can be an amino acid sequence derived from SEQ ID NO: 1 comprising the addition, substitution or modification of one or more amino acid residues. By way of illustration, functionally equivalent variants of the sequence SEQ ID NO: 1 include sequences comprising the addition of 1 amino acid, 2 amino acids, 3 amino acids, 4 amino acids, 5 amino acids, 10 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the amino terminus of the sequence SEQ ID NO: 1, and/or comprising the addition of 1 amino acid, 2 amino acids, 3 amino acids, 4 amino acids, 5 amino acids, 10 amino acids, 11 amino acids, 12 amino acids, 13 amino acids, 14 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the carboxy terminus of the sequence SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the activity of the sequence SEQ ID NO: 1.

The activity or function of the sequence SEQ ID NO: 1 and their functionally equivalent variants can be determined, by way of illustrative non-limitative example, assaying the protective ability against ischemia and/or ischemia reperfusion injury by a method shown in the present invention.

Functionally equivalent variants of SEQ ID NO: 1 also include amino acid sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequence SEQ ID NO: 1.

The terms "identity", "identical" or "percent identity" in the context of two or more amino acid sequences, refer to two or more sequences or subsequences that are the same or have a specified percentage of amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., 1990, Proc. Natl. Acad. Sci., 87:2264-8, as modified in Karlin et al., 1993, Proc. Natl. Acad. Sci., 90:5873-7, and incorporated into the NBLAST and XBLAST programs (Altschul et al., 1991, Nucleic Acids Res., 25:3389-402). In certain embodiments, Gapped BLAST can be used as described in Altschul et al., 1997, Nucleic Acids Res. 25:3389-402. BLAST-2, WU-BLAST-2 (Altschul et al., 1996, Methods in Enzymology, 266:460-80), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. 48:444-53 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-7 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second amino acid sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the global alignment taken the entirety of both sequences into consideration is used, therefore all letters and null in each sequence must be aligned. In this case, the same formula as above can be used but using as Z value the length of the region wherein the first and second sequence overlaps, said region having a length which is substantially the same as the length of the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-9 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of nucleotides in the reference sequence are allowed.

In some embodiments, two amino acid sequences are substantially identical, meaning they have at least 70%, at least 75%, at least 80%, at least 85%, at least 90%, and in some embodiments at least 95%, 96%, 97%, 98%, 99% amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared.

The compound according to the invention may be a polynucleotide encoding a polypeptide of SEQ ID NO: 1 or a functionally equivalent variant of said polypeptide.

The compound according to the invention may be a vector comprising a polynucleotide of the invention.

The term "vector", as used herein, refers to a nucleic acid sequence comprising the necessary sequences so that after transcribing and translating said sequences in a cell a polypeptide encoded by the polynucleotide of the invention is generated. Said sequence is operably linked to additional segments that provide for its autonomous replication in a host cell of interest. Preferably, the vector is an expression vector, which is defined as a vector, which in addition to the regions of the autonomous replication in a host cell, contains regions operably linked to the nucleic acid of the invention and which are capable of enhancing the expression of the products of the nucleic acid according to the invention. The vectors of the invention can be obtained by means of techniques widely known in the art.

Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Suitable vectors comprising a polynucleotide of the invention are vectors derived from expression vectors in prokaryotes such as pUC18, pUC19, pBluescript and their derivatives, mp18, mp19, pBR322, pMB9, ColE1, pCRI, RP4, phages and "shuttle" vectors such as pSA3 and pAT28, expression vectors in yeasts such as vectors of the 2-micron plasmid type, integration plasmids, YEP vectors, centromeric plasmids and similar, expression vectors in insect cells such as the vectors of the pAC series and of the pVL series, expression vectors in plants such as vectors of the series pIBI, pEarleyGate, pAVA, pCAMBIA, pGSA, pGWB, pMDC, pMY, pORE and similar and expression vectors in superior eukaryote cells based on viral vectors (adenovirus, virus associated to adenovirus as well as retrovirus and, in particular, lentivirus) as well as non-viral vectors such as pSilencer 4.1-CMV (Ambion), pcDNA3, pcDNA3.1/hyg, pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL, pKSV-10, pBPV-1, pML2d and pTDT1.

The compound according to the invention may also be a cell capable of secreting the polypeptide of the invention, a polypeptide of SEQ ID NO:1 or a functionally equivalent variant thereof.

Suitable cells capable of secreting a polypeptide of the invention include without limitation, cardiomyocytes, adipocytes, endothelial cells, epithelial cells, lymphocytes (B and T cells), mastocytes, eosinophils, vascular intima cells, primary cultures of isolated cells of different organs, preferably of cells isolated from Langerhans islets, hepatocytes, leukocytes, including mononuclear leukocytes, mesenchymal, umbilical cord or adult (of skin, lung, kidney and liver), osteoclasts, chondrocytes and other connective tissue cells. Cells of established lines such as Jurkat T cells, NIH-3T3, CHO, Cos, VERO, BHK, HeLa, COS, MDCK, 293, 3T3 cells, C2C12 myoblasts and W138 cells are also suitable. Persons skilled in the art will appreciate that the cells capable of secreting into the medium a polypeptide of the invention may be found forming microparticles or microcapsules so that the cells have a greater useful life in patients. Materials suitable for the formation of microparticles object of the invention include any biocompatible polymeric material which permits continuous secretion of the therapeutic products and which acts as support of the cells. Thus, said biocompatible polymeric material may be, for example, thermoplastic polymers or hydrogen polymers. Among the thermoplastic polymers we have acrylic acid, acrylamide, 2-aminoethyl methacrylate, poly(tetrafluoroethylene-cohexafluorpropylene), methacrylic-(7-cumaroxy) ethyl ester acid, N-isopropyl acrylamide, polyacrylic acid, polyacrylamide, polyamidoamine, poly(amino)-p-xylylene, poly(chloroethylvinylether), polycaprolactone, poly(caprolactone-co-trimethylene carbonate), poly(carbonate urea) urethane, poly(carbonate) urethane, polyethylene, polyethylene and acrylamide copolymer, polyethylene glycol, polyethylene glycol methacrylate, poly(ethylene terephthalate), poly(4-hydroxybutyl acrylate), poly(hydroxyethyl methacrylate), poly(N-2-hydroxypropyl methacrylate), poly(lactic glycolic acid), poly(L-lactic acid), poly(gamma-methyl, L-glutamate), poly(methylmethacrylate), poly(propylene fumarate), poly(propylene oxide), polypyrrole, polystyrene, poly(tetrafluoroethylene), polyurethane, polyvinyl alcohol, polyethylene of ultra-high molecular weight, 6-(p-vinylbenzamide)-hexanoic acid N-p-vinylbenzyl-D-maltonamide and copolymers containing more than one of said polymers.

Among the polymers of hydrogel type we have natural materials of alginate, agarose, collagen, starch, hyaluronic acid, bovine serum albumin, cellulose and their derivatives, pectin, chondroitin sulphate, fibrin and fibroin, as well as synthetic hydrogels such as Sepharose® and Sephadex®.

The compound of the invention may also be a nanoparticle comprising the polypeptide of the invention.

In another aspect, the compound of the invention may be a nanoparticle comprising the polynucleotide or the vector of the invention, The nanoparticles may contribute to preserve the integrity of the polypeptide in the biological fluids until it reaches the target organ. In addition, nanoparticles can also be modified so as to include moieties which allow the targeting of the nanoparticle to an organ of interest.

As used herein, a "nanoparticle" is a colloidal, polymeric, or elemental particle ranging in size from about 1 nm to about 1000 nm. Nanoparticles can be made up of silica, carbohydrate, lipid, or polymer molecules. Molecules can be either embedded in the nanoparticle matrix or may be adsorbed onto its surface. In one example, the nanoparticle may be made up of a biodegradable polymer such as poly(butylcyanoacrylate) (PBCA). Examples of elemental nanoparticles include carbon nanoparticles and iron oxide nanoparticles, which can then be coated with oleic acid (OA)-Pluronic®. In this approach, a drug (e.g., a hydrophobic or water insoluble drug) is loaded into the nanoparticle. Other nanoparticles are made of silica.

Nanoparticles can be formed from any useful polymer. Examples of polymers include biodegradable polymers, such as poly(butyl cyanoacrylate), poly(lactide), poly(glycolide), poly-ε-caprolactone, poly(butylene succinate), poly (ethylene succinate), and poly(p-dioxanone); poly(ethyleneglycol); poly-2-hydroxyethyl methacrylate (poly (HEMA)); copolymers, such as poly(lactide-co-glycolide), poly(lactide)-poly(ethyleneglycol), poly(poly(ethyleneglycol)cyanoacrylate-co-hexadecylcyanoacrylate, and poly [HEMA-co-methacrylic acid]; proteins, such as fibrinogen, collagen, gelatin, and elastin; and polysaccharides, such as amylopectin, a-amylose, and chitosan.

Other nanoparticles include solid lipid nanoparticles (SLN). Examples of lipid molecules for solid lipid nanoparticles include stearic acid and modified stearic acid, such as stearic acid-PEG 2000; soybean lecithin; and emulsifying wax. Solid lipid nanoparticles can optionally include other components, including surfactants, such as Epicuron® 200, poloxamer 188 (Pluronic® F68), Brij 72, Brij 78, polysorbate 80 (Tween 80); and salts, such as taurocholate sodium. Agents can be introduced into solid lipid nanoparticles by a number of methods discussed for liposomes, where such methods can further include high-pressure homogenization, and dispersion of microemulsions.

Nanoparticles can also include nanometer-sized micelles. Micelles can be formed from any polymers described herein. Exemplary polymers for forming micelles include block copolymers, such as poly(ethylene glycol) and poly(ε-caprolactone). (e.g., a PEO-b-PCL block copolymer including a polymer of ε-caprolactone and α-methoxy-ω-hydroxy-poly (ethylene glycol)).

In certain embodiments, the properties of the nanoparticles are altered by coating with a surfactant. Any biocompatible surfactant may be used, for example, polysorbate surfactants, such as polysorbate 20, 40, 60, and 80 (Tween 80); Epicuron® 200; poloxamer surfactants, such as 188 (Pluronic® F68) poloxamer 908 and 1508; and Brij surfactants, such as Brij 72 and Brij 78.

Nanoparticles can optionally be modified to include hydrophilic polymer groups (e.g., poly(ethyleneglycol) or poly(propyleneglycol)), for example, by covalently attaching hydrophilic polymer groups to the surface or by using polymers that contain such hydrophilic polymer groups (e.g., poly[methoxy poly (ethyleneglycol) cyanoacrylate-co-hexadecyl cyanoacrylate]). Nanoparticles can be optionally cross-linked, which can be particularly useful for protein-based nanoparticles.

Targeted delivery can be achieved by the addition of ligands without compromising the ability of nanoparticles to deliver their polypeptide payloads. It is contemplated that this will enable delivery to specific cells, tissues and organs. The targeting specificity of the ligand-based delivery systems are based on the distribution of the ligand receptors on different cell types. The targeting ligand may either be noncovalently or covalently associated with a nanoparticle, and can be conjugated to the nanoparticles by a variety of methods as discussed herein.

In another embodiment, the pharmaceutical composition of the invention is a nanoemulsion. "Nanoemulsion" as used herein means a colloidal dispersion of droplets (or particles) which at least some of the droplets have diameters in the nanometer size range. The nanoemulsions are comprised of omega-3, -6 or -9 fatty acid rich oils in an aqueous phase and thermo-dynamically stabilized by amphiphilic surfactants, which make up the interfacial surface membrane, produced using a high shear microfluidization process usually with droplet diameter within the range of about 80-220 nm.

In a preferred embodiment the pharmaceutical composition according to the invention further comprises
 a) a polypeptide of SEQ ID NO: 3 and/or SEQ ID NO: 4,
 b) a functionally equivalent variant of SEQ ID NO: 3 or SEQ ID NO: 4,
 c) a polynucleotide encoding a) or b),
 d) a vector comprising a polynucleotide according to c),
 e) a cell capable of secreting into the medium a polypeptide according to a) or b), and/or
 f) a nanoparticle comprising the polypeptide according to a) or b).

In a preferred embodiment, the pharmaceutical composition comprises a polypeptide of SEQ ID No: 1, and a polypeptide of SEQ ID NO: 3 and/or a polypeptide of SEQ ID NO: 4 or a functionally equivalent variant thereof.

SEQ ID NO: 3, as used herein, relates to GRP75, also known as HSPA9B, mt-HSP70 or mortalin, and refers to a chaperone assisting in the folding of other proteins in various intracellular compartments. The sequence of the protein GRP75 in humans corresponds to the sequence in the UniProt database P38646 17 Feb. 2016.

```
SEQ ID NO: 3:
MISASRAAAARLVGAAASRGPTAARHQDSWNGLSHEAFRLVSRRDYASEA

IKGAVVGIDLGTTNSCVAVMEGKQAKVLENAEGARTTPSVVAFTADGERL

VGMPAKRQAVTNPNNTFYATKRLIGRRYDDPEVQKDIKNVPFKIVRASNG

DAWVEAHGKLYSPSQIGAFVLMKMKETAENYLGHTAKNAVITVPAYFNDS

QRQATKDAGQISGLNVLRVINEPTAAALAYGLDKSEDKVIAVYDLGGGTF

DISILEIQKGVFEVKSTNGDTFLGGEDFDQALLRHIVKEFKRETGVDLTK

DNMALQRVREAAEKAKCELSSSVQTDINLPYLTMDSSGPKHLNMKLTRAQ

FEGIVTDLIRRTIAPCQKAMQDAEVSKSDIGEVILVGGMTRMPKVQQTVQ
```

```
                                                    -continued
DLFGRAPSKAVNPDEAVAIGAAIQGGVLAGDVTDVLLLDVTPLSLGIETL

GGVFTKLINRNTTIPTKKSQVFSTAADGQTQVEIKVCQGEREMAGDNKLL

GQFTLIGIPPAPRGVPQIEVTFDIDANGIVHVSAKDKGTGREQQIVIQSS

GGLSKDDIENMVKNAEKYAEEDRRKKERVEAVNMAEGIIHDTETKMEEFK

DQLPADECNKLKEEISKMRELLARKDSETGENIRQAASSLQQASLKLFEM

AYKKMASEREGSGSSGTGEQKEDQKEEKQ
```

SEQ ID NO: 4, as used herein, relates to PRDX6, or peroxiredoxin-6, a protein involved in redox regulation of the cell. The sequence of the protein peroxiredoxin-6 in humans corresponds to the sequence in the UniProt database P30041 17 Feb. 2016.

```
                                                       SEQ ID NO: 4
MPGGLLLGDVAPNFEANTTVGRIRFHDFLGDSWGILFSHPRDFTPVCTTE

LGRAAKLAPEFAKRNVKLIALSIDSVEDHLAWSKDINAYNCEEPTEKLPF

PIIDDRNRELAILLGMLDPAEKDEKGMPVTARVVFVFGPDKKLKLSILYP

ATTGRNFDEILRVVISLQLTAEKRVATPVDWKDGDSVMVLPTIPEEEAKK

LFPKGVFTKELPSGKKYLRYTPQP.
```

In another preferred embodiment the pharmaceutical composition of the invention comprises, consists essentially of or consist of SEQ ID NO: 1 and SEQ ID NO: 3; SEQ ID NO: 1 and SEQ ID NO: 4; SEQ ID NO: 3 and SEQ ID NO: 1; SEQ ID NO: 3 and SEQ ID NO: 4; SEQ ID NO: 4 and SEQ ID NO: 1; or SEQ ID NO: 4 and SEQ ID NO: 3, or any functionally equivalent variant thereof.

The definition of the term functionally equivalent variant of SEQ ID NO: 1 equally applies to the functionally equivalent variants of SEQ ID NO: 3 and SEQ ID NO: 4.

The activity or function of the sequence SEQ ID NO: 3 and their functionally equivalent variants can be determined by determining the cation-dependent ATPase activity or its chaperone activity, as known in the art.

The activity or function of the sequence SEQ ID NO: 4 and their functionally equivalent variants can be determined by assaying the glutathione peroxidase and phospholipase A2 activities, as known in the art.

The pharmaceutical composition according to the invention in addition to a compound a)-f) comprises a pharmaceutically acceptable excipient.

The terms "pharmaceutically acceptable excipient" or "pharmaceutically acceptable carrier", refer to any compound or combination of compounds that is essentially non-toxic to the subject at the dosage and concentration employed, and is compatible with the other components of a pharmaceutical composition. Thus, an excipient is an inactive substance formulated alongside the active ingredient of a pharmaceutical composition, for the purpose of bulking-up compositions that contain said active ingredients. Bulking up allows convenient and accurate dispensation of a drug substance when producing a dosage form. Excipients also can serve various therapeutic-enhancing purposes, such as facilitating compound (drug) absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients depends upon the route of administration and the dosage form, as well as the active ingredient and other factors. An excipient can be a non-toxic solid, semisolid or liquid filler, diluent, encapsulating material or formulation auxiliary of any conventional type. Illustrative, non-limitative, examples of excipients or carriers include water, salt (saline) solutions, alcohol, dextrose, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

In a particular embodiment, the pharmaceutical composition containing the compound for use in the present invention is a pharmaceutical composition for parenteral administration. Thus, said pharmaceutical composition suitable for parenteral injection, include physiologically acceptable sterile aqueous or non-aqueous solutions, dispersions, suspensions or emulsions, or may comprise sterile powders for reconstitution into sterile injectable solutions or dispersions. Examples of suitable aqueous or non-aqueous excipients or carriers, diluents, solvents or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. In a particular embodiment, the pharmaceutical composition containing the compound for use in the present invention is a pharmaceutical composition for intravenous, intramuscular or subcutaneous administration. Typically, pharmaceutical compositions for intravenous, intramuscular or subcutaneous administration are solutions in sterile isotonic aqueous buffer. If necessary, the pharmaceutical composition including the compound for use according to the invention also includes a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active ingredient. Where the pharmaceutical composition is to be administered by infusion, it can be dispensed with an infusion bottle containing sterile pharmaceutical grade water or saline. Where the pharmaceutical composition is administered by injection, an ampule of sterile water for injection or saline can be provided so that the ingredients may be mixed prior to administration.

In another particular embodiment, the pharmaceutical composition containing the compound for use in the present invention is a pharmaceutical composition for oral administration.

Solid dosage forms for oral administration include conventional capsules, sustained release capsules, conventional tablets, sustained-release tablets, chewable tablets, sublingual tablets, effervescent tablets, pills, suspensions, powders, granules and gels. In the solid dosage forms, the active ingredient (i.e., the compound selected from the group consisting of a) a polypeptide of SEQ ID NO:1; b) a functionally equivalent variant of the polypeptide according to a); c) a polynucleotide encoding a) or b); d) a vector comprising a polynucleotide according to c); e) a cell capable of secreting into the medium a polypeptide according to a) or b)), and f) a nanoparticle comprising the polypeptide according to a) or b) is admixed with at least one suitable excipient or carrier, such as sodium citrate or dicalcium phosphate or (a) fillers or extenders, such as for example, starches, lactose, sucrose, mannitol, or silicic acid; (b) binders, such as for example, carboxymethylcellulose, alginates, gelatin, polyvinylpyrrolidone, sucrose, or acacia; (c) humectants, such as for example, glycerol; (d) disintegrating agents, such as for example, agar-agar, calcium carbonate, potato or tapioca starch, alginic acid, certain complex silicates, or sodium carbonate; (e) solution retarding agents, such as for example, paraffin; (f) absorption accelerators, such as for example, quaternary ammonium compounds; (g) wetting agents, such as for example, cetyl alcohol or glycerol monostearate; (h) adsorbents, such as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents. Solid formulations of a similar type may also be used as fillers in soft or hard filled gelatin capsules using excipients such as lactose or milk sugar, as well as high molecular weight polyethylene glycols, and the like. Solid dosage forms such as coated tablets, capsules and granules can be prepared with coatings or shells, such as enteric coatings and others known in the art. They may also contain opacifying agents, and can be formulated such that they release the active ingredient or ingredients in a delayed manner. Examples of embedding formulations that can be used are polymeric substances and waxes. The active ingredients can also be in micro-encapsulated form, if appropriate, with one or more of the aforementioned excipients.

Liquid dosage forms for oral administration include pharmaceutically acceptable emulsions, solutions, suspensions, syrups and elixirs containing suitable excipients or carriers used in the art. In addition to the active ingredient (i.e., the compound selected from the group consisting of a) a polypeptide of SEQ ID NO:1; b) a functionally equivalent variant of the polypeptide according to a); c) a polynucleotide encoding a) or b); d) a vector comprising a polynucleotide according to c); e) a cell capable of secreting into the medium a polypeptide according to a) or b)) and f) a nanoparticle comprising the polypeptide according to a) or b) the liquid dosage form may contain one or more excipients or carriers commonly used in the art, such as water or other solvents, solubilizing agents and emulsifiers, such as for example, ethyl alcohol, isopropyl alcohol, ethyl carbonate, ethyl acetate, benzyl alcohol, benzyl benzoate, propylene glycol, 1,3-butylene glycol, dimethylformamide, oils, particular cottonseed oil, groundnut oil, corn germ oil, olive oil, castor oil, sesame seed oil, Miglyol®, glycerol, tetrahydrofurfuryl alcohol, polyethylene glycols, fatty acid esters of sorbitan, or mixtures of these substances, and the like. In addition to said inert diluents, the formulation can also include adjuvants, such as wetting agents, emulsifying and suspending agents, sweetening agents, flavoring agents and perfuming agents. Suspensions, in addition to the active ingredient or ingredients, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

In another particular embodiment, the pharmaceutical composition containing the compound for use in the present invention is a pharmaceutical composition for topical administration. For topical administration, said pharmaceutical composition can be formulated as a cream, gel, lotion, liquid, pomade, spray solution, dispersion, solid bar, emulsion, microemulsion and the like which may be formulated according to conventional methods that use suitable excipients, such as, for example, emulsifiers, surfactants, thickening agents, coloring agents and combinations of two or more thereof.

In another particular embodiment, the pharmaceutical composition can be formulated for use in a liquid used in the transportation of donor organs prior to transplant.

The pharmaceutical composition comprising a compound for use according to the invention may be also administered in the form of transdermal patches or iontophoresis devices. Thus, in a specific embodiment, a compound for use according to the invention is administered as a transdermal patch, for example, in the form of sustained-release transdermal patch. Suitable transdermal patches are described in more detail in, for example, U.S. Pat. Nos. 5,262,165, 5,948,433, 6,010,715 and 6,071,531.

Several drug delivery systems are known and can be used to administer the compounds for use according to the invention, including, for example, encapsulation in liposomes, microbubbles, emulsions, microparticles, microcapsules and the like. The required dosage can be administered as a single unit or in a sustained release form.

Sustainable-release forms and appropriate materials and methods for their preparation are described in the art. In a particular embodiment, the orally administrable form of a pharmaceutical composition comprising a compound for use according to the invention is in a sustained release form that further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of them. Enteric coatings may be applied using conventional processes known to experts in the art.

In a particular embodiment, when the compound for use according to the invention comprises a nucleic acid, the pharmaceutical composition may be formulated as a composition intended for use in gene therapy; by way of illustration, not limitation, that pharmaceutical composition may contain a viral or nonviral vector, which comprises the suitable polynucleotide or gene construction. By way of illustration and not limitation, said vectors, may be viral, for example, based on retrovirus, adenovirus, etc., or nonviral such as ADN-liposome, ADN-polymer, ADN-polymer-liposome complexes, etc. [see "Nonviral Vectors for Gene Therapy", edited by Huang, Hung and Wagner, Academic Press (1999)]. Said vectors, which contain the corresponding polynucleotide or gene construction, may be administered directly to a subject by conventional methods. Alternatively, said vectors may be used to transform, or transfect or infect cells, for example, mammal cells, including human, ex vivo, which subsequently will be implanted into a human body or an animal to obtain the desired therapeutic effect. For administration to a human body or an animal, said cells will be formulated in a suitable medium that will have no adverse influence on cell viability.

Those skilled in the art are familiar with the principles and procedures discussed are widely known.

Medical Uses

In an aspect, the present invention relates to a compound selected from the group consisting of:
a) a polypeptide of SEQ ID NO:1,
b) a functionally equivalent variant of the polypeptide according to a),
c) a polynucleotide encoding a) or b),
d) a vector comprising a polynucleotide according to c),
e) a cell capable of secreting into the medium a polypeptide according to a) or b), and f) a nanoparticle comprising the polypeptide according to a) or b)

or a pharmaceutical composition according to the invention for use in medicine.

In another aspect, the invention relates to a compound selected from the group consisting of:
a) a polypeptide of SEQ ID NO:1,
b) a functionally equivalent variant of the polypeptide according to a),
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

or a pharmaceutical composition according to the invention for use in the treatment and/or prevention of ischemia injury or ischemia/reperfusion injury in a subject.

Alternatively the invention relates to the use of a compound selected from the group consisting of:
a) a polypeptide of SEQ ID NO:1,
b) a functionally equivalent variant of the polypeptide according to a),
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

or the use of a pharmaceutical composition according to the invention for the preparation of a medicament for the treatment of ischemia injury or ischemia/reperfusion injury in a subject.

Alternatively, the invention relates to a method for treating and/or preventing ischemia injury or ischemia/reperfusion injury in a subject comprising administering a compound selected from the group consisting of:
a) a polypeptide of SEQ ID NO:1,
b) a functionally equivalent variant of the polypeptide according to a),
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

or administering a pharmaceutical composition according to the invention to the subject in need thereof.

In a particular embodiment, the pharmaceutical composition for use in medicine or for use in the treatment and/or prevention of ischemia or ischemia/reperfusion injury in a subject, further comprises
a) a polypeptide of SEQ ID NO: 3 and/or SEQ ID NO: 4,
b) a functionally equivalent variant of SEQ ID NO: 3 or SEQ ID NO: 4,
c) a polynucleotide encoding a) or b),
d) a vector comprising a polynucleotide according to c),
e) a cell capable of secreting into the medium a polypeptide according to a) or b), and/or
f) a nanoparticle comprising the polypeptide according to a) or b).

In another aspect, the invention relates to a compound selected from the group consisting of:
a) a polypeptide of SEQ ID NO:1,
b) a functionally equivalent variant of the polypeptide according to a), wherein the functionally equivalent variant is characterized in that it results from the deletion, substitution or modification of one of more amino acids of the sequence shown in SEQ ID NO:1 and wherein the functionally equivalent variant is not SEQ ID NO:2,
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

for use in the treatment and/or prevention of ischemia or ischemia/reperfusion injury in a subject.

In another aspect, the invention relates to a compound selected from the group consisting of
a) a polypeptide of SEQ ID NO:2,
b) a functionally equivalent variant of the polypeptide according to a), wherein the functionally equivalent variant is characterized in that it results from the deletion, substitution or modification of one of more amino acids of the sequence shown in SEQ ID NO: 2,
c) a polynucleotide encoding a) or b),
d) a vector comprising a polynucleotide according to c),
e) a cell capable of secreting into the medium a polypeptide according to a) or b), and
f) a nanoparticle comprising the polypeptide according to a) or b)

for use in the treatment of ischemia injury.

The term "administration", as used herein, relates to the delivery of a pharmaceutical drug to a subject. Suitable routes for administration of drugs include, without limitation, the parenteral (e.g., intradermal, intramuscular, intravenous, subcutaneous, etc.), enteral (e.g., oral, rectal, etc.), topical, etc., route.

The term "subject" or "individual" or "animal" or "patient", is meant any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

The term "treatment", as used herein, refers to both therapeutic measures and prophylactic or preventive measures, wherein the object is to prevent or slow down (lessen) an undesired physiological change or disorder, such as ischemia/reperfusion injury. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "prevention", as used herein, relates to the capacity to prevent, minimize or hinder the onset or development of a disease or condition before its onset.

"Ischemia", as used herein, relates to a restriction in blood supply to tissues or organs causing a shortage of oxygen and glucose needed for cellular metabolism.

The term "ischemia injury", as used herein, relates to the damage due to a shortage of oxygen and glucose needed for cellular metabolism.

The term "reperfusion", as used herein, relates to the restoration of blood flow to the ischemic tissue. Despite the unequivocal benefit of reperfusion of blood to an ischemic tissue, it is known that reperfusion itself can elicit a cascade of adverse reactions that paradoxically injure tissue.

The term "ischemia/reperfusion injury", as used herein, also known as "ischemia/reperfusion damage" relates to organ or tissue damage caused when blood supply returns to the organ or tissue after a period of ischemia. The absence of oxygen and nutrients from blood during the ischemic period creates a condition in which the restoration of circulation results in inflammation and oxidative damage through the induction of oxidative stress rather than restoration of normal function. Oxidative stress associated with reperfusion may cause damage to the affected tissues or organs. Ischemia/reperfusion injury is characterized biochemically by a depletion of oxygen during an ischemic event followed by reoxygenation and the concomitant generation of reactive oxygen species during reperfusion.

The injury that occurs with ischemia/reperfusion is the result of the interaction between the substances that accumulate during ischemia and those that are delivered on reperfusion. The cornerstone of these events is oxidative stress, defined as the imbalance between oxygen radicals and the endogenous scavenging system. The result is cell injury and death, which is initially localized, but eventually becomes systemic if the inflammatory reaction is unchecked.

According to the invention, the ischemia injury or ischemia/reperfusion injury is selected from the group comprising organ dysfunction (in the ischemic organ or in any other organ), infarct, inflammation (in the damaged organ or tissue), oxidative damage, mitochondrial membrane potential damage, apoptosis, reperfusion-related arrhythmia, cardiac stunning, cardiac lipotoxicity, ischemia-derived scar formation, and combinations thereof.

"Organ dysfunction" relates to a condition wherein a particular organ does not perform its expected function. An organ dysfunction develops into organ failure if the normal homeostasis cannot be maintained without external clinical intervention. Methods to determine organ dysfunction are known by the skilled person comprising, without limitation, monitorization and scores including sequential organ failure assessment (SOFA) score, multiple organ dysfunction (MOD) score and logistic organ dysfunction (LOD) score.

"Infarct" is defined later.

"Inflammation", or "inflammatory response", relates to a set of changes occurring in a tissue that undergoes inflammation. In particular, inflammation relates to the biological response to harmful stimuli, including pathogens, damaged cells or irritants. Methods to determine inflammation are known in the art and include, without limitation, measure of erythrocyte sedimentation rate (ESR), wherein a higher ESR is indicative of inflammation, measure of C-reactive protein (CRP), wherein a higher level of CRP is indicative of inflammation, and leukocyte count (increased in inflammation).

"Oxidative damage" relates to the biomolecular damage that can be caused by direct attack of reactive species during oxygen restoration. Oxidative damage may involve lipid peroxidation, oxidative DNA damage and oxidative damage to proteins. Methods to determine lipid peroxidation include, without limitation, MDA (malondialdehyde)-TBA (thiobarbituric acid) determination by HPLC, and quantification of isoprostanes (which are specific end products of the peroxidation of polyunsaturated fatty acids) by mass spectrometry. Methods to determine DNA oxidative damage include, without limitation, measure of 8-hydroxy-2'-deoxyguanosine (8OHdG). Methods to determine oxidative damage to proteins include, without limitation, quantification of individual aminoacid oxidation products including kynurenines (from tryptophan), bityrosine (which appears to be metabolically stable and can be detected in urine), valine and leucine hydroxides, L-dihydroxyphenylalanine (L-DOPA), ortho-tyrosine, 2-oxo-histidine, glutamate semialdehyde and adipic semialdehyde, as well as the carbonyl assay (involving measurement of protein carbonyl groups).

The "mitochondrial membrane potential ($\Delta\Psi m$) damage" relates to alterations in the membrane potential in the form of proton gradient across the mitochondrial inner membrane. Methods for evaluation of mitochondrial membrane potential damage are known by the skilled person and include the use of fluorescent probes for monitoring membrane potential including the JC1 dye (Cell Technology) and the measure of overall fluorescence at excitation and emission wavelengths allowing the quantification of green (485 nm and 535 nm) and red fluorescence (550 nm and 600 nm). Prolonged ischemia of any tissue or organ is known to induce mitochondrial membrane potential damage.

"Apoptosis" is related to a regulated network of biochemical events which lead to a selective form of cell suicide, and is characterized by readily observable morphological and biochemical phenomena, such as the fragmentation of the deoxyribonucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient. Methods to determine cell apoptosis are known by the skilled person and include, without limitation, assays that measure DNA fragmentation (including staining of chromosomal DNA after cell permeabilization), assays that measure the activation of caspases such as caspase 3 (including protease activity assays), assays that measure caspase cleavage products (including detection of PARP and cytokeratin 18 degradation), assays that examine chromatin chromatography (including chromosomal DNA staining), assays that measure DNA strand breaks (nicks) and DNA fragmentation (staggered DNA ends) (including active labeling of cell nick translation or ISNT and active labeling of cells by end labeling or TUNEL), assays that detect phosphatidylserine on the surface of apoptotic cells (including detection of translocated membrane component), assays that measure plasma membrane damage/leakage (including trypan blue exclusion assay and propidium iodide exclusion assay). Exemplary assays include analysis of scatter's parameters of apoptotic cells by flow cytometry, analysis of DNA content by flow cytometry (including DNA staining in a fluorochrome solution such as propidium iodide), fluorochrome labelling of DNA strand breaks by terminal deoxynucleotidyl transferase or TdT-assay, analysis of annexin-V binding by flow cytometry and TUNEL assay.

The ischemia injury or ischemia/reperfusion injury may also involve a reperfusion-related arrhythmia. "Arrhythmia", also known as cardiac dysrhythmia or irregular heartbeat, relates to a group of conditions in which the electrical activity of the heart is irregular, faster or slower, than normal. The heartbeat may be too fast (tachycardia, over 100 beats per minute) or too slow (bradycardia, less than 60 beats per minute), and may be regular or irregular. In some situations, arrhythmia may cause cardiac arrest. Arrhythmias can occur in the upper chambers of the heart (atria), or in the lower chambers of the heart (ventricles). Determination of arrhythmia is performed by the skilled in the art by means of electrocardiography (ECG).

"Cardiac stunning" involves different dysfunctional levels occurring after an episode of acute ischemia, despite blood flow is near normal or normal. After brief episodes of ischemia and reperfusion, prolonged mechanical dysfunction persists, although no histological signs of irreversible injury to cardiomyocytes exist, this phenomenon is called myocardial stunning. Stunning involves different facets: in addition to post-ischemic ventricular dysfunction myocardial (myocardial stunning), there is evidence of vascular/microvascular/endothelial injury (vascular stunning), post-ischemic metabolic dysfunction (metabolic stunning), long-lasting impairment of neurotransmission (neural/neuronal stunning), and electrophysiological alterations (electrical stunning).

"Cardiac lipotoxicity" involves a constellation of altered fatty acid metabolism, intramyocardial lipid overload and contractile dysfunction. Although it is unclear how lipids induce cardiac dysfunction, accumulation of intramyocardial triglyceride is associated with altered gene expression. Specifically, there is increased expression of the peroxisome proliferator-activated receptor α (PPARα)-regulated genes. PPARα is a nuclear receptor that, when activated by long chain fatty acids, induces the expression of proteins that increase the uptake and oxidation of fatty acids. Cardiac-specific overexpression of PPARα induces cardiac dysfunction in mice exposed to high circulating fatty acid levels. Pharmacologic activation of PPARα in the pressure-overloaded rat heart contributes to contractile dysfunction. In patients with diabetes and obesity, expression of the inflammatory cytokine tumor necrosis factor α (TNF-α) is increased in lipid-overloaded tissues and correlates positively with insulin resistance. TNF-α can directly cause contractile dysfunction in the heart and has been implicated in pathologic remodeling in heart failure. The accumulation of excess lipid within cardiomyocytes may lead to the production of toxic lipid intermediates, which can induce cell death.

"Scar" relates to any mark left on a tissue following the healing of a wound or damage. Particularly, this term related to the marks left in ischemic tissue. In the context of the invention, scar formation is derived from ischemia.

An ischemia injury or ischemia/reperfusion injury can be caused by a lot of causes, for example, by a natural event (e.g., restoration of blood flow following a myocardial infarction), a trauma, or by one or more surgical procedures or other therapeutic interventions that restore blood flow to a tissue or organ that has been subjected to a diminished supply of blood. Such surgical procedures include, for example, coronary artery bypass, graft surgery, coronary angioplasty, organ transplant surgery and the like (e.g., cardiopulmonary bypass surgery).

In a particular embodiment ischemia injury or ischemia/reperfusion injury is due to a condition selected from the group consisting of infarction, atherosclerosis, thrombosis, thromboembolism, lipid-embolism, bleeding, stent, surgery, angioplasty, end of bypass during surgery, organ transplantation, total ischemia, and combinations thereof.

"Infarct" or "infarction" relates to a localized area of ischemic necrosis produced by anoxia following occlusion of the arterial supply or venous drainage of a tissue or organ. More particularly, a myocardial infarction (MI), commonly known as heart attack, is related to an event by which blood stops flowing properly to part of the heart, and the heart muscle is injured due to not receiving enough oxygen. Usually an infarct is the result of blockage of one of the coronary arteries due to an unstable buildup of white blood cells, cholesterol and fat. Important risk factors are previous cardiovascular disease, old age, tobacco smoking, high blood levels of LDL cholesterol and triglycerides, low levels of HDL cholesterol, diabetes, high blood pressure, lack of physical activity, obesity, chronic kidney disease, excessive alcohol consumption, and the use of cocaine and amphetamines. Methods to determine whether a subject has suffered from infarction are known in the art and include, without limitation, tracing electrical signals in the heart by an electrocardiogram (ECG), and testing a blood sample for substances associated with heart muscle damage, including creatine kinase (CK-MB) and troponin. ECG testing is used to differentiate between two types of myocardial infarctions based on the shape of the tracing. An ST section of the tracing higher than the baseline is called an ST elevation MI (STEMI) which usually requires more aggressive treatment. Methods to determine infarct size are known by the skilled person and include measurement of serum markers including creatine kinase (CK)-MB levels in a serum sample (Grande P et al. 1982 Circulation 65: 756-764), tissue staining with triphenyl tetrazolium chloride (Fishbein M C et al. 1981 Am Heart J 101(5): 593-600), technetium (Tc)-99m sestamibi single-photon emission computed tomography (SPECT) myocardial perfusion imaging, and magnetic resonance.

"Atherosclerosis" relates to any hardening of arteries secondary to atheroma or accumulation in the artery walls that is made up of inflammatory cells (mostly macrophage cells) and cell debris, that contain lipids. The artery wall thickens as a result of the accumulation of calcium and fatty materials such as cholesterol and triglyceride. The elasticity of the artery walls is reduced, impairing blood flow.

"Thrombosis" relates to the formation of a blood clot or thrombus inside a blood vessel, obstructing the flow of blood through the circulatory system.

"Thromboembolism" relates to the formation in a blood vessel of a clot (thrombus) that breaks loose and is carried by the blood stream to plug another vessel. The clot may plug a vessel in the lungs (pulmonary embolism), brain (stroke), gastrointestinal tract, kidneys, or leg.

"Lipid-embolism" or "fat embolism" refers to the often asymptomatic presence of fat globules in the lung parenchyma and peripheral circulation after long bone or other major trauma.

"Bleeding" relates to the process of losing blood or having blood flow, especially surgically. In particular, internal bleeding occurs when there is damage to an artery or vein allowing blood to escape the circulatory system and collect inside the body. The internal bleeding may occur within tissues, organs, or in cavities of the body.

"Stent" relates to a dispositive such as a tube inserted into a natural passage/conduit in the body to prevent or counteract a disease-induced, localized flow constriction.

By "surgery" or "surgical treatment" is meant any therapeutic procedure that involves methodical action of the hand or of the hand with an instrument, on the body of a human or other mammal, to produce a curative or remedial.

"Angioplasty" relates to a technique of mechanically widening narrowed or obstructed arteries, the latter typically being a result of atherosclerosis. An empty and collapsed balloon on a guide wire, known as a balloon catheter, is passed into the narrowed locations and then inflated to a fixed size using water pressures some 75 to 500 times normal blood pressure (6 to 20 atmospheres). The balloon forces expansion of the inner white blood cell/clot plaque deposits and the surrounding muscular wall, opening up the blood vessel for improved flow, and the balloon is then deflated and withdrawn. A stent may or may not be inserted at the time of ballooning to ensure the vessel remains open.

"Bypass surgery" relates to a class of surgeries involving rerouting a tubular body part and includes cardiopulmonary bypass, partial ileal bypass surgery, ileojunal bypass, gastric bypass and vascular bypass such as coronary artery bypass surgery. Cardiopulmonary bypass (CBP) temporarily takes over the function of the heart and lungs during surgery, maintaining the circulation of blood and the oxygen content of the body. Partial ileal bypass surgery is a surgical procedure which involves shortening the ileum to shorten the total small intestinal length. The ileojejunal bypass is a surgery designed as a remedy for morbid obesity. A vascular bypass is a surgical procedure performed for inadequate or loss of blood flow to a region of the body. In particular, coronary artery bypass surgery, also known as coronary artery bypass graft (CABG) surgery, is a surgical procedure performed to relieve angina and reduce the risk of death from coronary artery disease.

By "transplantation" is meant a surgical procedure by which a cell, tissue or organ is transferred from a donor subject to a recipient subject or from one part of the body to another in the same subject. The "donor subject" is the subject who gives blood, cells, tissues, or an organ for another subject by blood transfusion or an organ transplant. The donor subject is a human or another mammal. The "recipient subject" is the subject who receives blood, cells, tissues, or an organ from another subject by blood transfusion or an organ transplant. The recipient subject is a human or another mammal. Transplanted tissues comprise, but are not limited to, bone tissue, tendons, corneal tissue, heart valves, veins and bone marrow. Transplanted organs comprise, but are not limited to, heart, lung, liver, kidney, pancreas and intestine. The particular surgical procedure of transplantation wherein the donor subject and the recipient subject are genetically non-identical members of the same species is known as allotransplantation. Thus, the term allotransplant (also known as allograft, allogeneic transplant or homograft) is related to the transplantation of cells, tissues or organs sourced from a genetically non-identical member of the same species as the recipient. The term "allotransplantable" refers to organs or tissues that are relatively often or routinely transplanted. Examples of allotransplantable organs include heart, lung, liver, pancreas, kidney and intestine. The particular surgical procedure of transplantation wherein the donor subject and the recipient subject are members of different species is known as xenotransplantation. Thus, the term xenotransplant (also known as xenograft, xenogeneic transplant or heterograft) is related to the transplantation of cells, tissues or organs sourced from a donor to a recipient, wherein donor and recipient are members of different species.

"Total ischemia" relates to ischemia in which arterial and/or venous blood supply are occluded.

The ischemia injury or ischemia/reperfusion injury to be prevented and/or treated according to the invention may occur in an organ or a tissue from a subject. Organs include, without limitation, brain, heart, kidneys, liver, large intestine, lungs, pancreas, small intestine, stomach, muscles, bladder, spleen, ovaries and testes. In a particular embodiment, the organ is selected from the group consisting of heart, liver, kidney, brain, intestine, pancreas, lung, skeletal muscle and combinations thereof. In a more particular embodiment, the organ is heart. Tissues include, without limitation, nerve tissue, muscle tissue, skin tissue and bone tissue.

In a particular aspect the ischemia injury or ischemia/reperfusion injury is due to myocardial infarction.

"Myocardial infarction" (MI) involves an ischemic necrosis of part of the myocardium due to the obstruction of one or several coronary arteries or their branches. Myocardial infarction is characterized by the loss of functional cardiomyocytes, the myocardial tissue being irreversibly damaged. The myocardium, or heart muscle, suffers an infarction when advanced coronary disease exists. In a particular case this occurs when an atheromatous plaque located inside a coronary artery ulcerates or ruptures, causing an acute obstruction of that vessel.

In a more particular embodiment, the ischemia injury or the ischemia/reperfusion injury is due to coronary obstruction (myocardial infarction) and further revascularization and blood re-flow.

According to the medical uses of the invention, a compound or a pharmaceutical composition of the invention are administered in a therapeutically effective amount.

The term "therapeutically effective amount", as used herein, in relation to the compound of the invention, or in relation to the compound, excipient and/or carrier comprised by the pharmaceutical composition of the invention, relates to the sufficient amount of said compound, excipient and/or carrier to provide the desired effect, i.e. to achieve an appreciable prevention, cure, delay, reduction of severity or amelioration of one or more symptoms derived from a disease, and will generally be determined by, among other causes, the characteristics of the agent itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated.

Even though individual needs vary, determination of optimal ranges for therapeutically effective amounts of the compounds for use according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the compound is administered as part of a combination of drugs. The amount of the compound for use according to the invention that is therapeutically effective in the prevention and/or treatment of ischemia injury or ischemia/reperfusion injury in a subject can be determined by conventional clinical techniques (see, for example, The Physician's Desk Reference, Medical Economics Company, Inc., Oradell, N J, 1995, and Drug Facts and Comparisons, Inc., St. Louis, Mo., 1993).

The dosage regimen for the compound for use according to the invention (i.e., the compound selected from the group consisting of a) a polypeptide of SEQ ID NO:1; b) a functionally equivalent variant of the polypeptide according to a); c) a polynucleotide encoding a) or b); d) a vector comprising a polynucleotide according to c); e) a cell capable of secreting into the medium a polypeptide according to a) or b), and f) a nanoparticle comprising the polypeptide according to a) or b) or the pharmaceutical composition of the invention can vary within a broad range.

In a preferred embodiment the compound or pharmaceutical composition for use according to the invention is administered prior to ischemia. In another preferred embodiment, the compound or pharmaceutical composition for use according to the invention is administered prior to reperfusion. In another embodiment, the compound or pharmaceutical composition for use according to the invention is administered after ischemia and prior to reperfusion. In another embodiment, the compound or pharmaceutical composition for use according to the invention is administered during ischemia, preferably during ischemia and prior to reperfusion.

More preferably, the compound or pharmaceutical composition for use according to the invention is administered at a period of time which can vary broadly; nevertheless, in a particular embodiment, the compound is administered at least 1 second prior to ischemia or reperfusion, typically at least 15, 30 or 45 seconds prior to reperfusion, preferably at least 1 minute, 5 minutes, 10 minutes, 15 minutes, 30 minutes, 45 minutes prior to ischemia or reperfusion, or even at least 1 hour, 2 hours or 3 hours prior to ischemia or reperfusion or even before.

The compound or pharmaceutical composition for use according to the invention, can be administered to a subject by any suitable route of administration, for example, parenteral (e.g., intramuscular, intravenous, subcutaneous, etc.), enteral (i.e., oral, rectal, etc.), etc.

In a preferred embodiment, the compound or pharmaceutical composition for use according to the invention, is administered parenterally, more preferably by intravenous route.

The vectors of the invention, which contain the corresponding polynucleotide of the invention, may be administered directly to a subject by conventional methods. Alternatively, said vectors may be used to transform, or transfect or infect cells, for example, mammal cells, including human, ex vivo, which subsequently will be implanted into a human body or an animal to obtain the desired therapeutic effect. For administration to a human body or an animal, said cells will be formulated in a suitable medium that will have no adverse influence on cell viability.

Those skilled in the art are familiar with the principles and procedures discussed in widely known and available sources as Remington's Pharmaceutical Science (17th Ed., Mack Publishing Co., Easton, Pa., 1985), Goodman and Gilman's The Pharmaceutical Basis of Therapeutics (8th Ed., Pergamon Press, Elmsford, N.Y., 1990) and "Tratado de Farmacia Galénica", C. Fauli and Trillo, Luzán 5, S.A. de Ediciones, 1993 and in Remington's Pharmaceutical Sciences (A. R. Gennaro, Ed.), 20$^{th}$ edition, Williams & Wilkins PA, USA (2000).

In another preferred embodiment, the subject to be treated or prevented from ischemia injury or ischemia/reperfusion injury shows low level of expression of Gprc5a or low activation of the Gprc5a signaling pathway in the organ or tissue suffering ischemia injury and/or ischemia/reperfusion injury.

In another preferred embodiment, the subject to be treated or prevented from ischemia injury or ischemia/reperfusion injury has been selected by showing low level of expression of Gprc5a or low activation of the Gprc5a signaling pathway in the organ or tissue suffering ischemia injury and/or ischemia/reperfusion injury.

In another preferred embodiment, the subject to be treated or prevented from ischemia injury or ischemia/reperfusion injury has been selected by a method comprising determining the level of Gperc5a or the level of activation of the Gprc5a signaling pathway in the organ or tissue suffering ischemia injury and/or ischemia/reperfusion injury. In this case, the subject to be treated is selected if shows low level of expression of Gprc5a or low activation of the Gprc5a signaling pathway in the organ or tissue suffering ischemia injury and/or ischemia/reperfusion injury.

In another preferred embodiment, the level of Gperc5a or the level of activation of the Gprc5a signaling pathway is determined in the organ or tissue which suffers ischemia injury or ischemia/reperfusion injury.

"Gprc5a" (G Protein-Coupled Receptor, Class C, Group 5, Member A, retinoic acid-induced protein 3), as used herein, relates to a gene that encodes a member of the type 3 G protein-coupling receptor family, characterized by the signature 7-transmembrane domain motif. The sequence of the protein Gprc5a in humans corresponds to the sequence in the Uniprot database Q8NFJ5 9 Dec. 2015.

"Low level of expression", relates to a level of expression of Gprc5a gene which is lower than a reference value. The expression level is considered to be lower than a reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested. In a preferred embodiment the reference value corresponds to the level of activation of Gperc5a signaling in a subject not suffering ischemia injury and/or ischemia/reperfusion injury. In another preferred embodiment, the reference value corresponds to the level of activation of Gperc5a signaling in a healthy subject.

Methods for detecting the expression can be based on detecting Gprc5a mRNA or protein, or they also can be based on determining the mRNA levels or protein levels and the levels of variants thereof, in a sample as a whole, in cells of a sample and/or in the non-cellular fraction of a sample.

Methods for detecting mRNA are well known in the art and include, e.g., real-time PCR (rtPCR), northern blotting, nanostring and microarray technologies. Alternatively, it is also possible to determine the expression levels of Gprc5a gene by means of the determination of the expression levels of the protein encoded by said gene, since if the expression of genes is increased, an increase of the amount of corresponding proteins should occur and if the expression of genes is decreased, a decrease of the amount of corresponding proteins should occur. The methods for determining the level of expression of a gene are widely known in the art.

The activation of Gprc5a signaling pathway, may be determined by any method known in the art, for example by detecting the levels of PI3K/Akt/NF-KB, PKC and/or Rho.

All the terms and embodiments previously described in relation to the pharmaceutical composition are equally applicable to this aspect of the invention.

The invention is detailed below by means of the following examples which are merely illustrative and by no means limiting the scope of the invention.

Materials & Methods

Myocardial Ischemia/Reperfusion Porcine Experimental Model and Echocardiography

Twenty-six farm swine (Landrace-Largewhite cross, 36-39 kg) were acclimated for 1 week before any experimental procedure. Thereafter, animals were randomized to the following three groups: Group-I) closed-chest 1.5 h left anterior descending (LAD) coronary occlusion with no reperfusion (Ischemia; n=10); Group-II) 1.5 h LAD occlusion followed by 2.5 h reperfusion (IdR; n=5); Group-III) 1.5 h LAD occlusion followed by ischemic post-conditioning and then 2.5 h reperfusion (IPostCo; n=5) (Vilahur G. et al., Eur Heart J 2012; 34:2082-2093). The IPost-Co protocol was induced by 6 cycles of 20 seconds of reperfusion and 20 seconds of reocclusion at the onset of reperfusion as previously reported (Vilahur G. et al., cited supra).

A sham-operated group of animals was included (Group-IV; sham; n=6).

The study protocol was approved by the institutional ethics committee (CSIC-ICCC) and all animal procedures were performed conform the guidelines from Directive 2010/63/EU of the European Parliament on the protection of animals used for scientific purposes or the NIH guidelines, and following the ARRIVE guidelines (Kilkenny C PLoS biology 2010; 8:e1000412).

Twelve hours prior to the experimental induction of acute myocardial infarction (AMI), as previously described (Vilahur G. et al., cited supra), a loading dose of clopidogrel was administered to all animals. Angiographic images were used to guide angioplasty balloon placement (below the first diagonal branch) and occlusion/reperfusion. Heart rate and ECG were monitored throughout the surgical procedure. The inventors used 2D echocardiograms (Phillips iE33) to assess global cardiac function (i.e., left ventricle ejection fraction, LVEF) in all animals before coronary occlusion (at baseline), 1.5 h post-occlusion just before reperfusion, and at the end of the reperfusion period (sacrifice) (Vilahur G. et al., cited supra).

At the end of the experimental period, Evan's Blue dye was injected in anesthetized animals (coronary sinus) to outline the area-at-risk (AAR) after which the hearts were arrested and excised. Tissue from the AAR was obtained for further molecular, proteomic and confocal microscopy studies of the ischemic myocardium (Vilahur G. et al., cited supra). Infarct size was evaluated by triphenyl tetrazolium chloride (TTC) staining.

TUNEL Staining

Apoptosis assessment in the ischemic myocardium was performed by dUTP nick-end labelling (TUNEL) using an apoptosis detection kit according to the manufacturer's protocol (Chemicon Inc.). Apoptosis rate was expressed as percentage of the number of TUNEL-positive cardiomyocytes/total cells per field (mean 5 fields/animal).

Murine Model of Myocardial Infarction

The study was performed in male CH3 mice 8-10 weeks old weighing 25-30 g (Jackson Laboratory). Mice were randomly given an intraperitoneal injection of 50 µg DJ-1 (full length recombinant human DJ-1, MBS143125, >95% purity (n=10); or truncated recombinant DJ-1 (DJ-1-17) lacking the last 15 amino acids of the C-terminal domain of the protein, MBS717208, >90% purity (n=9)); or equal PBS volume for vehicle/controls (n=25) 60 min prior LAD coronary artery ligation, that was performed as previously reported (Bayes-Genis A. et al., J Mol Cell Cardiol 2010; 49:771-80) for 45 min. Then, animals were sacrificed (Ischemia; n=15 PBS, n=5 DJ-1 and n=5 DJ-1-17) or reperfused for 2 h (IdR; n=10 PBS, n=5 DJ-1 and n=4 DJ-1-17) and then sacrificed. Afterwards hearts were carefully excised for morphometric assessment of infarct size (Takagawa J. et al., Journal of applied physiology 2007; 102:2104-11), quantification of leukocyte infiltration and validation of murine gene expression changes. A sham-operated group of animals (N=4) following the same operating procedure without ischemia was included.

Rat Model of Myocardial Infarction

The study was performed in male SD rats 8-10 weeks old weighing 250-300 g (Jackson Laboratory). MI was induced by LAD coronary artery ligation, that was performed as previously reported (Bayes-Genis A. et al., J Mol Cell Cardiol 2010; 49:771-80) for 45 min. After 10 min of ischemia rats were randomly given an intraperitoneal injection of 0.86 mg/kg of DJ-1-17 (truncated recombinant human DJ-1 lacking the last 15 amino acids of the C-terminal domain of the protein, >90% purity (n=7); or equal PBS volume for vehicle/controls (n=7). Thirty five minutes after DJ-1-17 administration (after 45 min of ischemia) animals were sacrificed (Ischemia; n=4 PBS and n=4 DJ-1-17) or reperfused for 7 days (IdR; n=3 PBS, n=3 DJ-1-17) and then sacrificed. Afterwards hearts were carefully excised for morphometric assessment of infarct size (Takagawa J. et al., Journal of applied physiology 2007; 102:2104-11).

Proteomic, Transcriptomic and in Silico Bioinformatics Analysis

Protein extracts from the ischemic myocardium were separated by 2-DE (n=3/group) and protein spots of interest were identified by MALDI-TOF/TOF as previously described (Vilahur G. et al., cited supra).

The myocardial gene expression changes in the mouse model of ischemia/reperfusion with/without DJ-1 administration were analyzed by using a platform (GeneChip Mouse Gene 1.0ST; Affymetrix) to identify the potential pathways involved in DJ-1-mediated cardioprotection. Raw data are deposited in NCBI's Gene Expression Omnibus (accession number: GSE66307) (Edgar R, et al., Nucleic acids research 2002; 30:207-10). The statistically significant networks and canonical pathways were analyzed through the use of IPA (Ingenuity Systems, www.ingenuity.com).

Selected markers were validated by real-time PCR (Nos2, Gprc5, caspase-3, and SOD2), western blot (p53 phosphorylated on Thr155) and immunohistochemistry analysis (DJ-1, iNOS, 8-hydroxyguanosine (8HOG), and cleaved-caspase-3).

Statistical Analysis

Continuous variables are expressed as median and interquartile range unless stated. Statistical analyses were performed by non-parametric Kruskal Wallis (multiple comparisons without adjustment) and Mann-Whitney test (differences between groups). Correlations were determined by Spearman correlation. All statistical analyses were two Example 1—IPost-Co Improves Cardiac Global Performance The study comprised the following three groups: Group-I) closed-chest 1.5 h LAD coronary occlusion with no reperfusion (Ischemia; n=10); Group-II) 1.5 h LAD occlusion followed by 2.5 h reperfusion (IdR; n=5); Group-III) 1.5 h LAD occlusion followed by ischemic post-conditioning and then 2.5 h reperfusion (IPostCo; n=5). The IPost-Co protocol was induced by 6 cycles of 20 seconds of reperfusion and 20 seconds of reocclusion at the onset of reperfusion as previously reported. A sham-operated group of animals following the same operating procedure but without ischemia was included (Group-IV; sham; n=6). Benefits of IPost-Co were measured by clinical and morphological evaluation of heart function and infarct size reduction after 2.5 h of reperfusion. As previously published (Vilahur G. et al., cited supra), in this animal model of maximal ischemic stimuli, ischemia markedly and similarly diminished global cardiac performance (LVEF) in all animals by 38 [36-43]% visualized by a marked septo-apical akinesia. No further significant changes were detected 2.5 h post-reperfusion (36 [33-38]%); however, IPost-Co resulted in a 10% amelioration in LVEF with respect to all other groups. Mean heart rate was similar among the different animal groups and remained constant throughout the procedure (75 [72-76]-73 [70-76]%). In myocardial samples of these animals, the inventors investigated the mechanisms behind that significant clinical improvement applying a proteomic systems biology approach.

Example 2—Proteomes of the Ischemic, Reperfused and Post-Conditioned Myocardium

Three hundred and six spots were consistently detected in the myocardial tissue extracts of the area at risk (AAR) of ischemia. Twenty eight of the identified spots corresponded to 29 nonredundant mitochondrial-related proteins.

Example 3—In-Silico Bioinformatics Analysis

Bioinformatics analysis of the identified proteins revealed that the mitochondrial dysfunction and apoptosis canonical pathway was significantly modified among the differentially treated groups (P<0.0001). Complexes I, III and V were significantly affected. Moreover, the proteomic signatures belonged to proteins of the cell death and survival network (P<0.0001).

When mitochondrial dysfunction related proteins were analyzed in ischemic myocardium compared to non-ischemic myocardium of sham-operated animals (effect of ischemia) differentially affected proteins were mainly down-regulated and localized in complexes I (NADH dehydrogenase), III (cytochrome bc1 complex), and V (ATP synthase) of the respiratory chain of the mitochondria (P<0.0001). When the same analysis was performed to understand the effect of reperfusion, comparing results after direct reperfusion and after ischemia (effect of reperfusion) the same complexes were affected (P<0.0001) mainly showing a down-regulation in complexes I and II, a down-regulation in the beta subunit of complex V and an up-regulation in the alpha subunit of the ATP synthase. To identify effects of IPost-Co, comparisons were made between myocardium of animals subjected to IPost-Co and to ischemia; and between IPost-Co myocardium and direct reperfusion. In both cases an up-regulation of proteins in the three complexes was detected (P<0.0001). When compared to sham-operated animals, IPost-Co showed an up-regulation in proteins of complexes I and III and a decrease in proteins of complex V, while direct reperfusion down-regulated complexes I, III, and V as compared with sham operated animals.

Example 4—IPost-Co Reverts Ischemia-Induced Changes by Inducing Antioxidant Mitochondrial-Related Proteins in the Myocardium The myocardium of ischemia and ischemia/reperfusion animals showed a decrease in 15 mitochondrial related proteins, whereas IPost-Co normalized over 47% of those changes by inducing an increase in 20 mitochondrial related proteins.

Among the identified differential proteins, the only protein with both cytoplasmic and mitochondrial localizations, which was one of the most affected by IPost-Co, was protein DJ-1.

Figure 1:
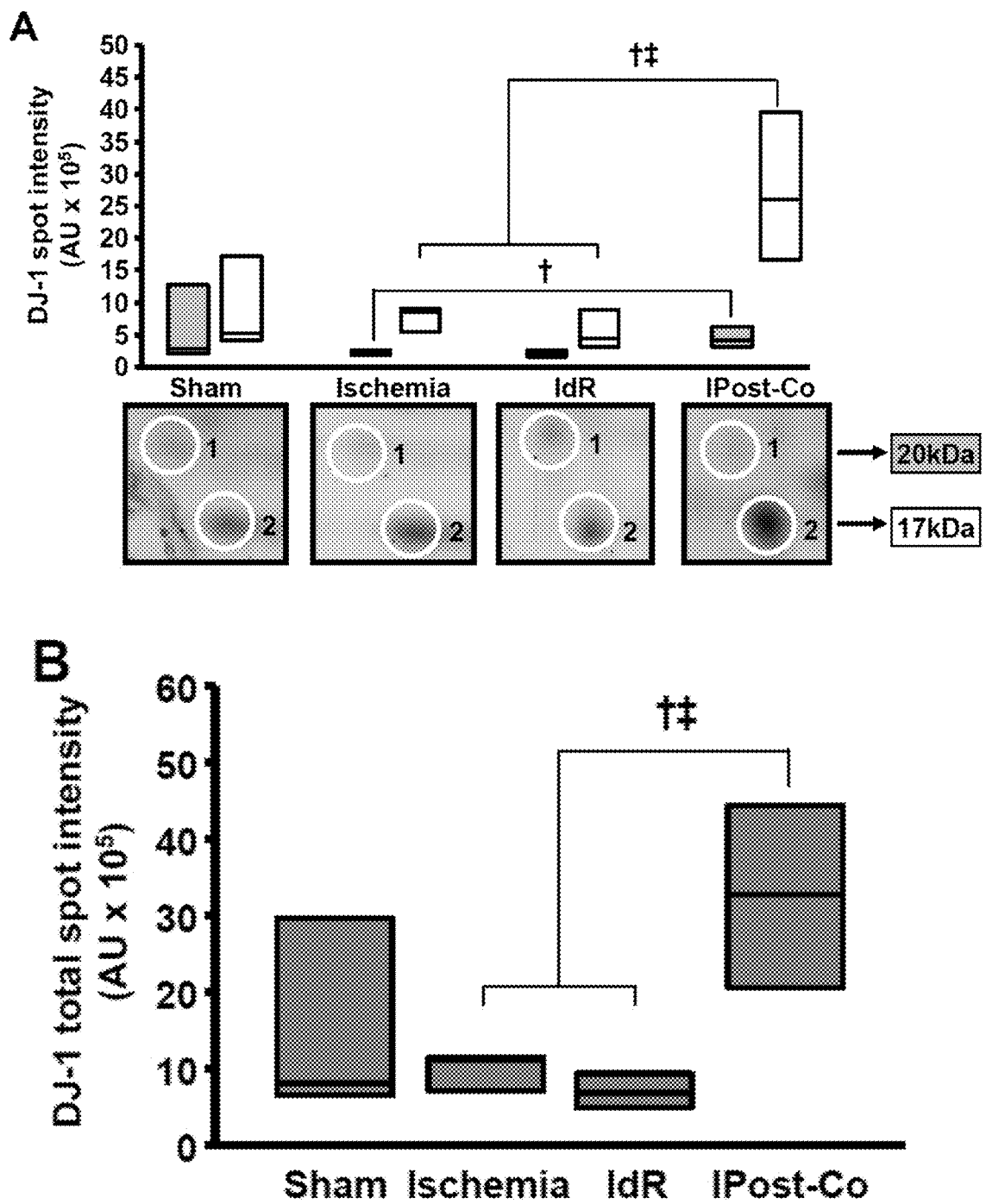
FIG. 1. Changes in protein DJ-1. Box plots showing changes in (A) DJ-1 spots intensity, and (B) DJ-1 total intensity (†P<0.05 IPost-Co vs. ischemia; ‡P<0.05 IPost-Co vs. IdR; Mann-Whitney; n≥3/group). (C) Box plot showing changes in DJ-1 gene expression levels (*P<0.001 Kruskal-Wallis; § P<0.05 vs. sham-operated animals; †P<0.05 vs. ischemia; and ‡P<0.05 vs. IdR; Mann-Whitney; n≥5/group).
Figure 1:
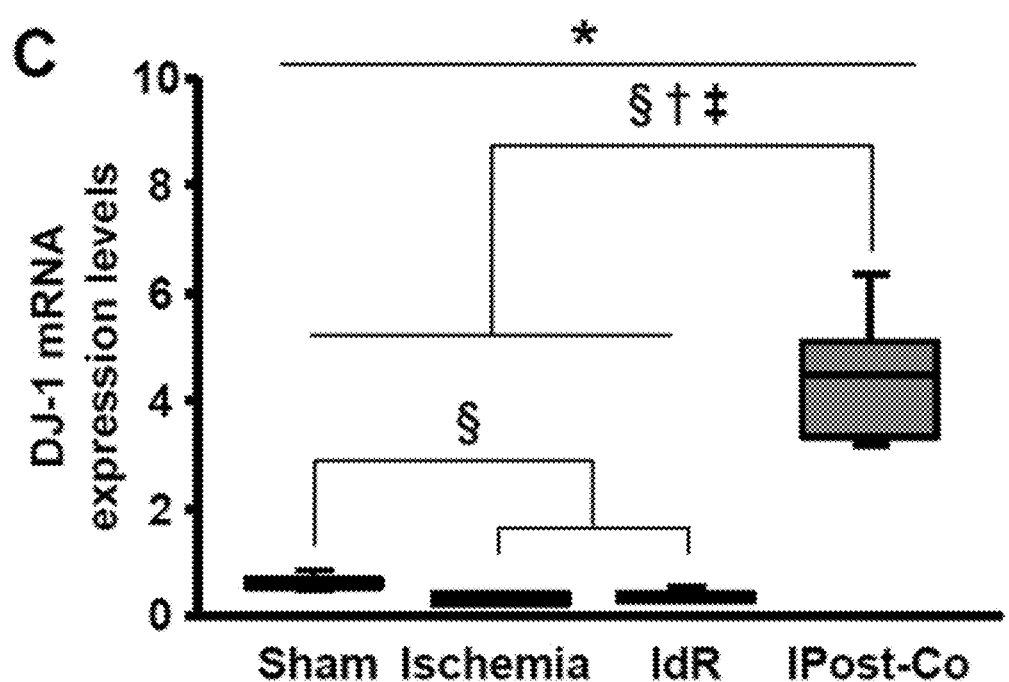

DJ-1 was identified in the myocardial proteome as two spots, one of 20 kDa, corresponding to full length DJ-1, and another of 17 kDa (FIG. 1A). Total DJ-1 intensity was significantly higher in the myocardium of IPost-Co animals than in ischemic hearts (IPost-Co: 33 [25-41] vs. I: 11 [8.6-12]; P<0.05) and in those hearts with direct reperfusion (IdR: 6.9 [5.6-8.6]; P<0.05; FIG. 1B). The highest levels were detected in the 17 kDa form that showed a 6-fold increase when compared to IdR (IPost-Co: 26 [20-35] vs. IdR: 4.4 [3.5-7.3]; P<0.05) and to ischemia alone (I: 8.6 [6.5-8.9]; P<0.05; FIG. 1A).

DJ-1 gene expression was evaluated by rt-PCR in the myocardial tissue samples of the same animals. DJ-1 gene expression was highly regulated by the procedures investigated (P<0.001; FIG. 10). Specifically, both ischemia and direct reperfusion induced a significant reduction in DJ-1 gene transcription when compared to sham-operated animals (S: 0.55 [0.52-0.65] vs. I: 0.31[0.25-0.38]; and vs. IdR: 0.33 [0.29-0.41]; P<0.05 for both comparisons). IPost-Co induced a significant increase in DJ-1 gene expression when compared not only to I and IdR (IPost-Co: 4.49 [3.35-4.72]; P<0.05 for both comparisons), but also to sham-operated animals (P<0.05).

Figure 2:
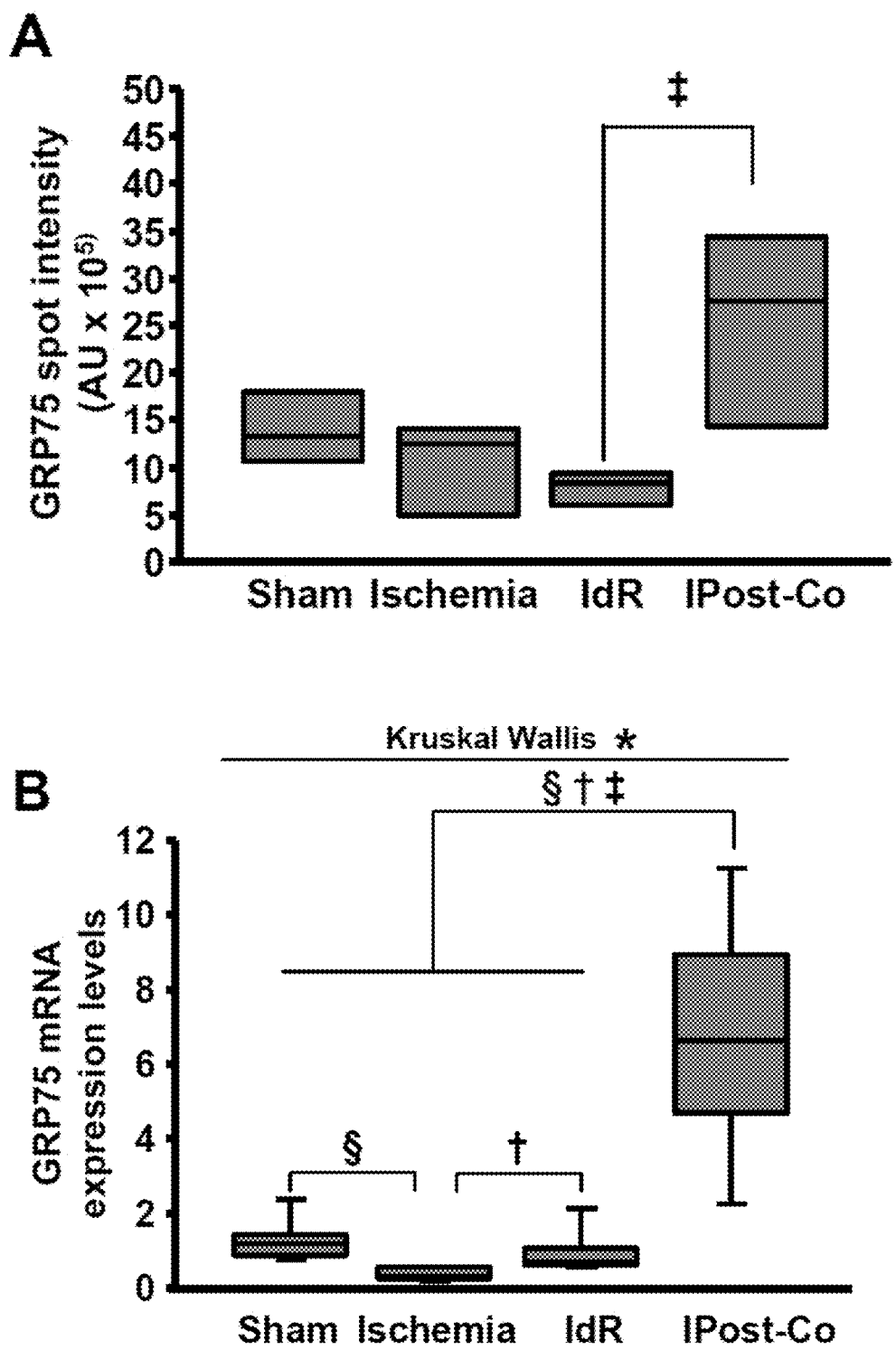
FIG. 2. Changes in protein GRP75 and peroxiredoxin-6. Box plot showing changes between groups in GRP75 (A) spot intensity (‡P<0.05 IPost-Co vs. IdR; Mann-Whitney; n≥3/group); and (B) gene expression levels (*P<0.001
Figure 2:
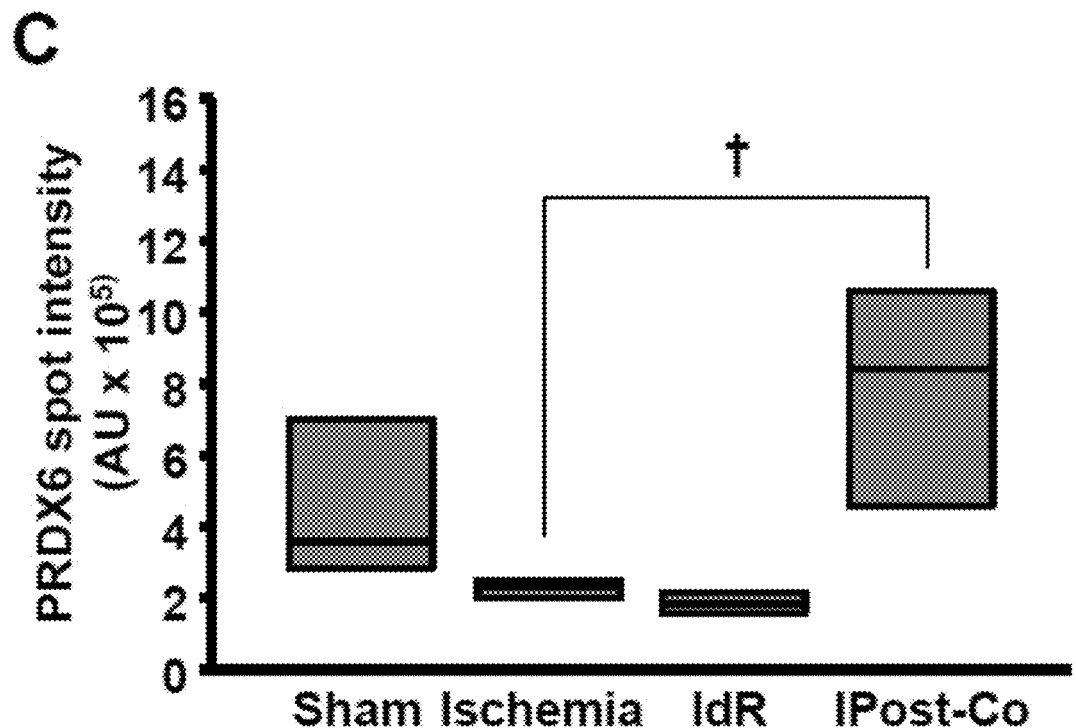
Figure 2:
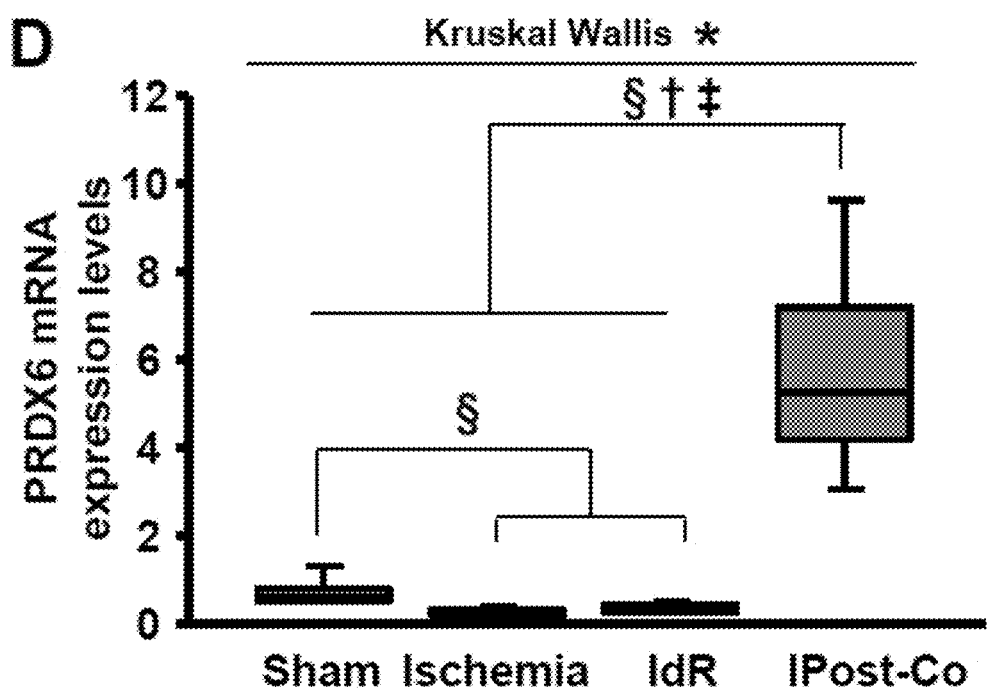

IPost-Co also affected a DJ-1 related stress-response protein, GRP75 (also named mortalin or stress-70 protein mitochondrial). This protein was identified as a single spot with a pI of 5.9 and a molecular weight of 74 kDa. No significant changes were induced by I nor by IdR, however, hearts treated by IPost-Co showed a 3.3-fold higher level of GRP75 intensity when compared to IdR animals (IPost-Co: 28 [19-32] vs. IdR: 8.3 [6.8-9.0]; P<0.05; FIG. 2A). Interestingly, GRP75 gene expression also showed important changes associated to the interventions (P<0.0001; FIG. 2B). Ischemia induced a significant down-regulation in GRP75 gene transcription when compared to sham-operated animals (I: 0.34 [0.25-0.53] vs. S: 1.19 [0.96-1.38]; P<0.05). Whereas, IdR induced a slight but significant increase in GRP75 gene transcription when compared to ischemic hearts (IdR: 0.67 [0.66-0.69]; P<0.05). The strongest change was detected in the IPost-Co group (IPost-Co: 6.60 [5.50-8.16]) that showed that GRP75 gene transcription was significantly up-regulated when compared to ischemic myocardium (P<0.05), IdR (P<0.05), and sham-operated animals (P<0.05).

Peroxiredoxin-6, a known antioxidant protein, showed as well a significant increase in the myocardium of hearts treated with IPost-Co when compared to ischemic hearts (IPost-Co: 8.4 [5.9-9.9] vs. I: 2.3 [2.1-2.4]; P<0.05; FIG. 2C). Peroxiredoxin-6 gene transcription was also affected by the interventions (P<0.001; FIG. 2D). Peroxiredoxin-6 expression was significantly down-regulated by ischemia and direct reperfusion when compared to myocardium of sham operated animals (S: 0.60 [0.52-0.78] vs. I: 0.29 [0.21-0.34]; and vs. IdR: 0.33 [0.29-0.4]; P<0.05 for both comparisons). On the contrary, peroxiredoxin-6 gene transcription was significantly upregulated by IPost-Co (IPost-Co: 5.22 [4.52-6.36]; P<0.05 vs. I, IdR and sham-operated animals).

In order to test if the observed changes in those stress-related proteins in relation to the different reperfusion strategies could be affecting the levels of oxidative stress in the ischemic myocardium the inventors analyzed by immunohistochemical analysis the myocardial content of 8-hydroxyguanosine (8HOG), a known marker of DNA oxidative stress damage. Animals subjected to IdR showed an important increase in 8HOG levels in the ischemic myocardium when compared with sham-operated animals (P<0.05; FIGS. 3A and 3B). On the contrary, animals subjected to IPost-Co showed lower 8HOG values, comparable to those of sham-operated animals (P<0.05 vs. I and IdR; FIGS. 4A and 4B). Myocardial levels of 8HOG were inversely correlated with the content of the three stress-related proteins, DJ-1 (FIG. 3C), GRP75 (FIG. 3D) and PRDX6 (FIG. 3E) in the ischemic myocardium, highlighting the direct role of these proteins in oxidative stress regulation.

Additionally, the inventors evaluated the levels of phosphorylated p53 by western blot in the ischemic myocardium as an indicator of oxidative stress-related cell death (FIG. 4A). Phosphorylated p53 levels were significantly increased in animals subjected to IdR when compared to animals subjected to ischemia alone (P<0.05). Whereas, IPost-Co significantly reduced phosphorylated p53 levels in the myocardium when compared to direct reperfusion (P<0.05). Total DJ-1 (FIG. 4B) and GRP75 (FIG. 4C) protein levels in the ischemic myocardium were inversely and significantly correlated with phosphorylated p53 levels.

Example 5—Increased DJ-1 and GRP75 Detection in Myocardial Tissue after IPost-Co Next the inventors performed a confocal microscopy analysis of myocardial tissue sections staining for mitochondria and DJ-1. DJ-1 was mainly localized in the cytoplasm in sham-operated animals and in animals subjected to ischemia and direct reperfusion. Instead, there was a strong increase in DJ-1 mitochondrial localization in the myocardium of IPost-Co treated animals.

Similarly, GRP75 was mainly localized in the cytoplasm in sham-operated animals and in animals subjected to ischemia and direct reperfusion. IPost-Co treated animals also showed a strong increase in GRP75 mitochondrial localization in the myocardium.

Example 6—Systemic Administration of DJ-1 Protects Against IdR Injury

As a proof of principle mice were pre-treated with recombinant DJ-1 protein (50 µg i.p. 1 h before intervention) in a double-blind study design (blind for interventional operator and for anatomopathological analysis). Animals were subjected to 45 min of ischemia by ligation of the LAD. Computer assisted morphometric assessment revealed that pre-treatment with DJ-1 reduced the infarct size after ischemia (FIG. 5A). DJ-1 treated animals showed infarcts 25% smaller than placebo treated controls after ischemia. Interestingly, infarct size in animals subjected to ischemia and reperfusion showed a 75% reduction after DJ-1 treatment (P<0.05). The increase in DJ-1 myocardial content in the DJ-1 treated groups was confirmed by immunohistochemistry. The DJ-1-mediated protective effect on infarct size reduction was associated with a decrease in the infiltration of both neutrophils and macrophages to undetectable levels (P<0.05; FIGS. 6A and 6B, respectively).

Example 7—Transcriptomic Analysis of DJ-1 Effects in the Myocardium

The myocardium of mice exposed to ischemia/reperfusion was analyzed by transcriptomics to identify the most affected genes. DJ-1 administration before ischemia and direct reperfusion induced a multigenic response when compared to placebo treated animals as depicted in the heat map by clearly differentiated gene clusters. Among the detected changes, DJ-1 induced a differential transcriptomic signature in G protein-coupled receptors such as Gprc5a. Indeed, the in silico systems biology analysis of the differentially expressed genes after DJ-1 pre-treatment revealed significant changes in the Gaq-signaling canonical pathway.

The canonical pathway involved in NO and ROS production in macrophages was also modified by DJ-1 pre-treatment.

Furthermore, DJ-1 treated mice revealed a 1.2-fold decrease in the gene expression of the apoptosis effector caspase-7 (P=0.008), together with a 1.3-fold increase in the expression of the anti-apoptotic factor Bcl2a1d after IdR when compared with those subjected to IdR without DJ-1 pre-treatment (P=0.003).

The observed changes in gene expression of G protein-coupled receptor Gprc5a were validated by rt-PCR. Gprc5a gene expression showed a 1.7-fold significant increase in DJ-1 pre-treated animals subjected to reperfusion compared to the placebo group (P<0.05; FIG. 7A). The influence of DJ-1 pre-treatment in the canonical pathway involved in NO production was also validated, as a significant decrease in Nos2 gene expression was evidenced in the myocardial tissue of DJ-1 treated mice (1.6-fold decrease; P<0.05; FIG. 7B).

The observed changes in apoptosis were validated by the analysis by rt-PCR of caspase-3 gene expression levels, as an important effector of apoptosis execution. DJ-1 treatment induced a significant reduction in caspase-3 gene expression when compared to IdR animals without DJ-1 (P=0.01; FIG. 7C). Similarly, DJ-1 treatment also induced a significant decrease in the myocardial content of cleaved caspase-3 in mice subjected to IdR when compared to placebo animals (P<0.05; FIG. 8A). Furthermore, DJ-1 administration was able to significantly reduce the percentage of TUNEL positive cells observed by confocal microscopy in the mouse model of IdR (P=0.009; FIG. 8B).

Example 8—Antioxidant Effects of DJ-1 Treatment in the Myocardium

In order to test the effects of DJ-1 treatment in the oxidative stress-related pathway the inventors analyzed by immunohistochemistry the content of iNOS and 8HOG in mice myocardium. DJ-1 administration was able to reduce the high levels of both iNOS (FIG. 9A) and 8HOG (FIG. 9B)

observed after ischemia and reperfusion. There was an inverse and significant association between DJ-1 and iNOS contents (FIG. 9C) and between DJ-1 and 8HOG levels (FIG. 9D) in the myocardium. The myocardial content of iNOS was directly and significantly associated to 8HOG levels (FIG. 9E). Thus the immunohistochemical analysis validated the obtained data in the array gene expression analysis and highlighted the involvement of the iNOS oxidative stress pathway in the DJ-1-mediated protection against myocardial injury.

No effect was observed in SOD2 gene expression levels after DJ-1 treatment in DJ-1 pre-treated animals subjected to reperfusion when compared to the placebo group (P=0.248).

Example 9—Systemic Administration of DJ-1-17 Truncated Form Exerts Higher Protection Against Myocardial Ischemia As the results of the proteomic analysis revealed that the strongest change DJ-1 levels in the myocardium in response to IPost-Co were observed in a 17 kDa variant of DJ-1 (FIG. 1A), the inventors investigated whether the administration of a DJ-1 truncated variant of 17 kDa exerted additional cardioprotective effects as compared to that observed after administration of the full length DJ-1 peptide. To this aim the inventors synthesized a truncated variant of DJ-1 lacking the last 15 amino acids of the C-terminal domain of the protein (DJ-1-17). The administration of DJ-1-17 in the same experimental conditions exerted a stronger protective effect against ischemia by inducing a 86% mean reduction in infarct size when compared to that observed in DJ-1 treated animals (P=0.04; FIG. 10). The protective effect in animals subjected to ischemia and direct reperfusion was similar after pre-treatment with DJ-1-17 and DJ-1 (64% and 76% mean reduction in infarct size respectively; P=NS; FIG. 10).

Example 10—Systemic Administration of DJ-1-17 Protects Against Acute Ischemia and Long Term IdR Injury As a proof of concept and in order to demonstrate its potential therapeutic value in the clinical setting rats were treated with recombinant DJ-1-17 protein (0.86 mg/kg i.p.) once ischemia was established (after 10 min of LAD coronary artery ligation) in a double-blind study design (blind for interventional operator and for anatomopathological analysis). Animals were subjected to a total of 45 min of ischemia. Computer assisted morphometric assessment revealed that treatment with DJ-1-17 reduced the infarct size after ischemia (FIG. 11A). DJ-1-17 treated animals showed infarcts 44% smaller than placebo treated controls after ischemia (P=0.04). Interestingly, infarct size in animals subjected to ischemia and 7 days of reperfusion also showed a 35% mean reduction after DJ-1-17 treatment (FIG. 11B; P=0.08). These results highlight the potential therapeutic value of DJ-1-17 treatment to reduce acute ischemic injury after the onset of MI and that its protective effects are maintained on the long-term.

The invention claimed is:

1. A pharmaceutical composition comprising the DJ-1-17 polypeptide consisting of SEQ ID NO: 1 or a functionally equivalent variant thereof having at least 97% sequence identity with the DJ-1-17 polypeptide consisting of SEQ ID NO: 1, the GRP75 polypeptide consisting of SEQ ID NO: 3 or a functionally equivalent variant thereof having at least 97% sequence identity with the GRP75 polypeptide consisting of SEQ ID NO: 3, and/or the PRDX6 polypeptide consisting of SEQ ID NO: 4 or a functionally equivalent variant thereof having at least 97% sequence identity with the PRDX6 polypeptide consisting of SEQ ID NO: 4, and a pharmaceutically acceptable excipient.

2. The pharmaceutical composition according to claim 1 comprising the DJ-1-17 polypeptide consisting of SEQ ID NO: 1, the GRP75 polypeptide consisting of SEQ ID NO: 3, and the PRDX6 polypeptide consisting of SEQ ID NO: 4.

3. A method for the treatment and/or prevention of ischemia or ischemia/reperfusion injury in a subject comprising the administration to said subject the DJ-1-17 polypeptide consisting of SEQ ID NO: 1 or a functionally equivalent variant thereof having at least 97% sequence identity with the DJ-1-17 polypeptide consisting of SEQ ID NO:1.

4. The method according to claim 3, wherein the ischemia or ischemia/reperfusion injury is due to a condition selected from the group consisting of infarction, atherosclerosis, thrombosis, thromboembolism, lipid-embolism, bleeding, stent, surgery, angioplasty, end of bypass during surgery, organ transplantation, total ischemia, and combinations thereof.

5. The method according to claim 3 wherein the ischemia or ischemia/reperfusion injury is produced in an organ or a tissue selected from the group consisting of heart, liver, kidney, brain, intestine, pancreas, lung, skeletal muscle and combinations thereof.

6. The method according to claim 3 wherein the ischemic injury or ischemia/reperfusion injury is selected from the group comprising organ dysfunction, infarct, inflammation, oxidative damage, mitochondrial membrane potential damage, apoptosis, reperfusion-related arrhythmia, cardiac stunning, cardiac lipotoxicity, ischemia-derived scar formation, and combinations thereof.

7. The method according to claim 3 wherein the ischemic or ischemia/reperfusion injury is due to myocardial infarction.

8. The method according to claim 3, wherein the polypeptide is administered prior to ischemia.

9. The method according to claim 3, wherein said polypeptide is administered during ischemia or prior to reperfusion.

10. The method according to claim 3 wherein the polypeptide is administered parenterally.

11. The method according to claim 3 wherein the subject shows low level of expression of Gprc5a with respect to the level of expression of Gpcrc5a in a subject not suffering ischemia and/or ischemia/reperfusion injury or the subject shows low activation of the Gprc5a signaling pathway in the organ or tissue suffering ischemic and/or ischemia/reperfusion injury with respect to the level of activation of Gpcrc5a signaling in a subject not suffering ischemia and/or ischemia/reperfusion injury.

12. The method of claim 3, wherein the method comprises administration to said subject the DJ-1-17 polypeptide consisting of SEQ ID NO: 1.

13. The method according to claim 12 wherein the ischemia or ischemia/reperfusion injury is due to a condition selected from the group consisting of infarction, atherosclerosis, thrombosis, thromboembolism, lipid-embolism, bleeding, stent, surgery, angioplasty, end of bypass during surgery, organ transplantation, total ischemia, and combinations thereof.

14. The method according to claim 12 wherein the ischemia or ischemia/reperfusion injury is produced in an organ or a tissue selected from the group consisting of heart, liver, kidney, brain, intestine, pancreas, lung, skeletal muscle and combinations thereof.

15. The method according to claim 12 wherein the ischemic injury or ischemia/reperfusion injury is selected from the group comprising organ dysfunction, infarct, inflammation, oxidative damage, mitochondrial membrane potential damage, apoptosis, reperfusion-related arrhythmia, cardiac stunning, cardiac lipotoxicity, ischemia-derived scar formation, and combinations thereof.

16. The method according to claim 12 wherein the ischemic or ischemia/reperfusion injury is due to myocardial infarction.

17. The method according to claim 12, wherein the polypeptide is administered prior to ischemia.

18. The method according to claim 12, wherein said polypeptide is administered during ischemia or prior to reperfusion.

19. The method according to claim 12 wherein the polypeptide is administered parenterally.

20. The method according to claim 12 wherein the subject shows low level of expression of Gprc5a with respect to the level of expression of Gpcrc5a in a subject not suffering ischemia and/or ischemia/reperfusion or the subject shows low activation of the Gprc5a signaling pathway in the organ or tissue suffering ischemic and/or ischemia/reperfusion injury with respect to the level of activation of Gpcrc5a signaling in a subject not suffering ischemia and/or ischemia/reperfusion injury.

21. A method for the treatment and/or prevention of ischemia or ischemia/reperfusion injury in a subject comprising the administration to said subject of a pharmaceutical composition according to claim 1.

22. A method for the treatment and/or prevention of ischemia or ischemia/reperfusion injury in a subject comprising the administration to said subject of a pharmaceutical composition comprising the DJ-1 polypeptide consisting of SEQ ID NO: 2 or a functionally equivalent variant thereof having at least 97% sequence identity with the DJ-1 polypeptide consisting of SEQ ID NO: 2, the GRP75 polypeptide consisting of SEQ ID NO: 3 or a functionally equivalent variant thereof having at least 97% sequence identity with the GRP75 polypeptide consisting of SEQ ID NO: 3, and/or the PRDX6 polypeptide consisting of SEQ ID NO: 4 or a functionally equivalent variant thereof having at least 97% sequence identity with the PRDX6 polypeptide consisting of SEQ ID NO: 4, and a pharmaceutically acceptable excipient.

* * * * *

SEQUENCE LISTING

```
<160> NUMBER OF SEQ ID NOS: 4

<210> SEQ ID NO 1
<211> LENGTH: 174
<212> TYPE: PRT
<213> ORGANISM: Homo sapiens

<400> SEQUENCE: 1

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly
                165                 170
```

```
<210> SEQ ID NO 2
<211> LENGTH: 189
<212> TYPE: PRT
<213> ORGANISM: Homo sapiens

<400> SEQUENCE: 2

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
                20                  25                  30

Val Thr Val Ala Gly Leu Ala Gly Lys Asp Pro Val Gln Cys Ser Arg
            35                  40                  45

Asp Val Val Ile Cys Pro Asp Ala Ser Leu Glu Asp Ala Lys Lys Glu
        50                  55                  60

Gly Pro Tyr Asp Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185

<210> SEQ ID NO 3
<211> LENGTH: 679
<212> TYPE: PRT
<213> ORGANISM: Homo sapiens

<400> SEQUENCE: 3

Met Ile Ser Ala Ser Arg Ala Ala Ala Arg Leu Val Gly Ala Ala
1               5                   10                  15

Ala Ser Arg Gly Pro Thr Ala Ala Arg His Gln Asp Ser Trp Asn Gly
                20                  25                  30

Leu Ser His Glu Ala Phe Arg Leu Val Ser Arg Arg Asp Tyr Ala Ser
            35                  40                  45

Glu Ala Ile Lys Gly Ala Val Val Gly Ile Asp Leu Gly Thr Thr Asn
        50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140
```

```
Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285

Glu Phe Lys Arg Glu Thr Gly Val Asp Leu Thr Lys Asp Asn Met Ala
    290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
        355                 360                 365

Ala Met Gln Asp Ala Glu Val Ser Lys Ser Asp Ile Gly Glu Val Ile
    370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
        435                 440                 445

Thr Leu Gly Gly Val Phe Thr Lys Leu Ile Asn Arg Asn Thr Thr Ile
    450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
        515                 520                 525

Ile Val His Val Ser Ala Lys Asp Lys Gly Thr Gly Arg Glu Gln Gln
    530                 535                 540

Ile Val Ile Gln Ser Ser Gly Gly Leu Ser Lys Asp Asp Ile Glu Asn
545                 550                 555                 560
```

```
Met Val Lys Asn Ala Glu Lys Tyr Ala Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
        595                 600                 605

Asn Lys Leu Lys Glu Glu Ile Ser Lys Met Arg Glu Leu Leu Ala Arg
    610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

Asp Gln Lys Glu Glu Lys Gln
        675

<210> SEQ ID NO 4
<211> LENGTH: 224
<212> TYPE: PRT
<213> ORGANISM: Homo sapiens

<400> SEQUENCE: 4

Met Pro Gly Gly Leu Leu Leu Gly Asp Val Ala Pro Asn Phe Glu Ala
1               5                   10                  15

Asn Thr Thr Val Gly Arg Ile Arg Phe His Asp Phe Leu Gly Asp Ser
            20                  25                  30

Trp Gly Ile Leu Phe Ser His Pro Arg Asp Phe Thr Pro Val Cys Thr
        35                  40                  45

Thr Glu Leu Gly Arg Ala Ala Lys Leu Ala Pro Glu Phe Ala Lys Arg
    50                  55                  60

Asn Val Lys Leu Ile Ala Leu Ser Ile Asp Ser Val Glu Asp His Leu
65                  70                  75                  80

Ala Trp Ser Lys Asp Ile Asn Ala Tyr Asn Cys Glu Glu Pro Thr Glu
                85                  90                  95

Lys Leu Pro Phe Pro Ile Ile Asp Asp Arg Asn Arg Glu Leu Ala Ile
            100                 105                 110

Leu Leu Gly Met Leu Asp Pro Ala Glu Lys Asp Glu Lys Gly Met Pro
        115                 120                 125

Val Thr Ala Arg Val Val Phe Val Phe Gly Pro Asp Lys Lys Leu Lys
    130                 135                 140

Leu Ser Ile Leu Tyr Pro Ala Thr Thr Gly Arg Asn Phe Asp Glu Ile
145                 150                 155                 160

Leu Arg Val Val Ile Ser Leu Gln Leu Thr Ala Glu Lys Arg Val Ala
                165                 170                 175

Thr Pro Val Asp Trp Lys Asp Gly Asp Ser Val Met Val Leu Pro Thr
            180                 185                 190

Ile Pro Glu Glu Glu Ala Lys Lys Leu Phe Pro Lys Gly Val Phe Thr
        195                 200                 205

Lys Glu Leu Pro Ser Gly Lys Lys Tyr Leu Arg Tyr Thr Pro Gln Pro
    210                 215                 220
```